(12) United States Patent
Roncancio et al.

(10) Patent No.: US 9,804,178 B2
(45) Date of Patent: Oct. 31, 2017

(54) MATERIALS AND METHODS FOR RAPID AND SPECIFIC DETECTION OF COCAINE

(71) Applicants: Daniel Roncancio, Miami, FL (US); Haixiang Yu, Miami, FL (US); Xiaowen Xu, Miami, FL (US); Yi Xiao, Miami, FL (US)

(72) Inventors: Daniel Roncancio, Miami, FL (US); Haixiang Yu, Miami, FL (US); Xiaowen Xu, Miami, FL (US); Yi Xiao, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 14/930,242

(22) Filed: Nov. 2, 2015

(65) Prior Publication Data
US 2016/0131668 A1    May 12, 2016

Related U.S. Application Data

(60) Provisional application No. 62/073,718, filed on Oct. 31, 2014.

(51) Int. Cl.
| | |
|---|---|
| *C07H 21/02* | (2006.01) |
| *C07H 21/04* | (2006.01) |
| *G01N 33/94* | (2006.01) |
| *C12N 15/115* | (2010.01) |
| *A61K 31/70* | (2006.01) |

(52) U.S. Cl.
CPC ......... *G01N 33/946* (2013.01); *C12N 15/115* (2013.01); *C12N 2310/16* (2013.01); *C12N 2320/10* (2013.01)

(58) Field of Classification Search
None
See application file for complete search history.

(56) References Cited

U.S. PATENT DOCUMENTS

| | | | |
|---|---|---|---|
| 8,735,367 B2* | 5/2014 | Heemstra | G01N 33/946 435/6.1 |
| 8,933,210 B2* | 1/2015 | Lu | C07H 21/02 435/6.1 |

OTHER PUBLICATIONS

Roncancio et al. Analytical Chemistry, vol. 86:11100-11106, 2014.*
Kang, Kyungho et al., "Aptamer Functionalized Microcantilever Sensors for Cocaine Detection," *Langmuir*, 2011, 27:14696-14702.
Liu, Juewen et al., "Fast Colorimetric Sensing of Adenosine and Cocaine Based on a General Sensor Design Involving Aptamers and Nanoparticles," *Angew. Chem. Int. Ed.*, 2006, 45:90-94.
Stojanovic, Milan N. et al., "Aptamer-Based Folding Fluorescent Sensor for Cocaine," *Journal of the American Chemical Society*, May 2001, 123(21):4928-4931.
Zheng, Dongmei et al., "Label-Free Fluorescent Detection of Ions, Proteins, and Small Molecules Using Structure-Switching Aptamers, SYBR Gold, and Exonuclease I," *Anal. Chem.*, 2012, 84:3554-3560.
Baker, Brian R. et al., "An Electronic, Aptamer-Based Small-Molecule Sensor for the Rapid, Label-Free Detection of Cocaine in Adulterated Samples and Biological Fluids," *J. Am. Chem. Soc.*, 2006, 128:3138-3139.
Du, Yan et al., "G-Quadruplex-based DNAzyme for colorimetric detection of cocaine: Using magnetic nanoparticles as the separation and amplification element," *Analyst*, 2011, 136:493-497.
He, Jing-Lin et al., "Fluorescence Aptameric Sensor for Strand Displacement Amplification Detection of Cocaine," *Anal. Chem.*, 2010, 82:1358-1364.
Stojanovic, Milan N. et al., "Aptamer-Based Colorimetric Probe for Cocaine," *J. Am. Chem. Soc.*, 2002, 124:9678-9679.
Stojanovic, Milan N. et al., "Fluorescent Sensors Based on Aptamer Self-Assembly," *J. Am. Chem. Soc.*, 2000, 122:11547-11548.

* cited by examiner

*Primary Examiner* — Sean McGarry
(74) *Attorney, Agent, or Firm* — Saliwanchik, Lloyd & Eisenchenk

(57) ABSTRACT

The invention pertains to a rapid and specific aptamer-based method for one-step cocaine detection with minimal reagent requirements based on an aptamer sensor that reports the presence of cocaine via the displacement and unquenching of a bound fluorophore molecule. In certain embodiments, the invention provides novel aptamers, which have reduced background fluorescence, bind a fluorophore molecule tightly, and show an increased signal gain in the presence of cocaine.

18 Claims, 21 Drawing Sheets

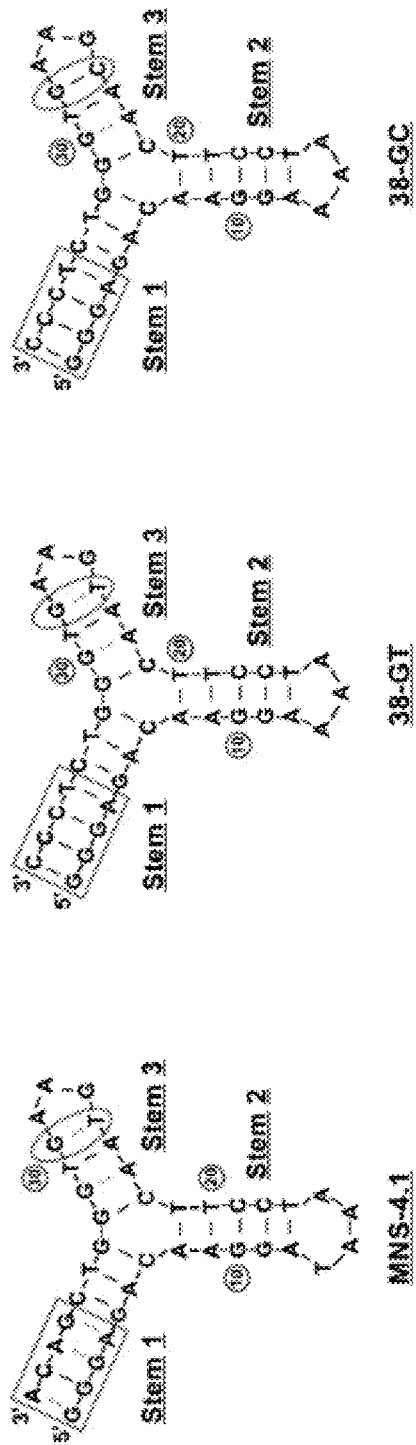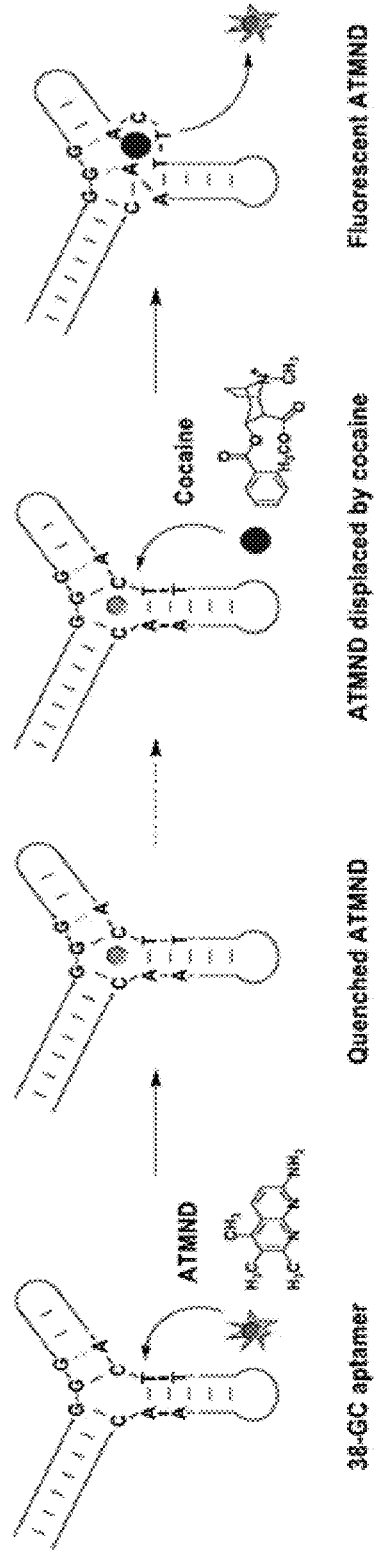
FIG. 1A  FIG. 1B  FIG. 1C
FIG. 2A  FIG. 2B  FIG. 2C  FIG. 2D

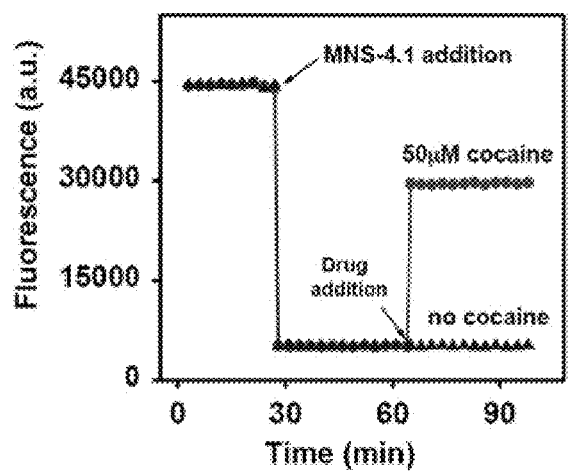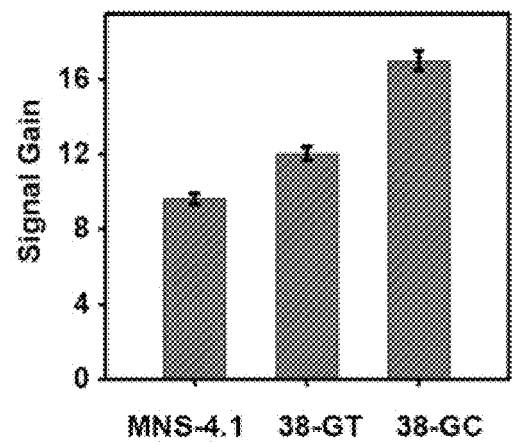
FIG. 3A  FIG. 3B
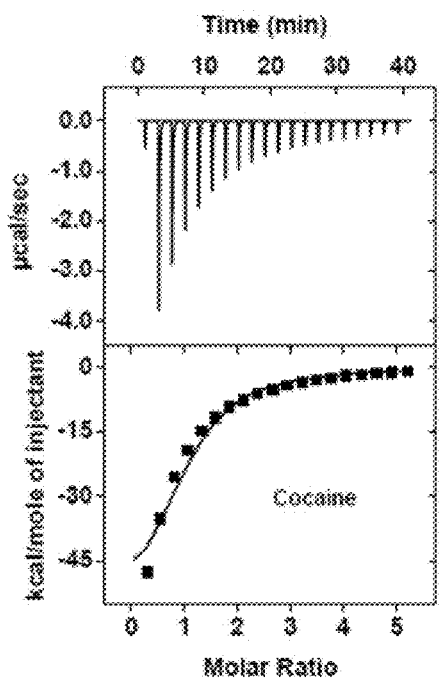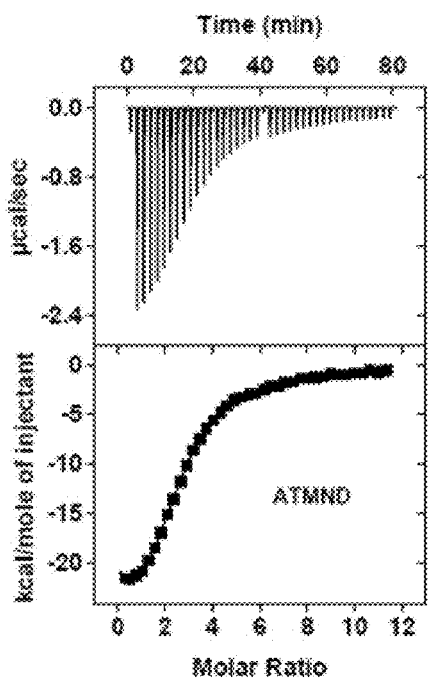
FIG. 4A  FIG. 4B

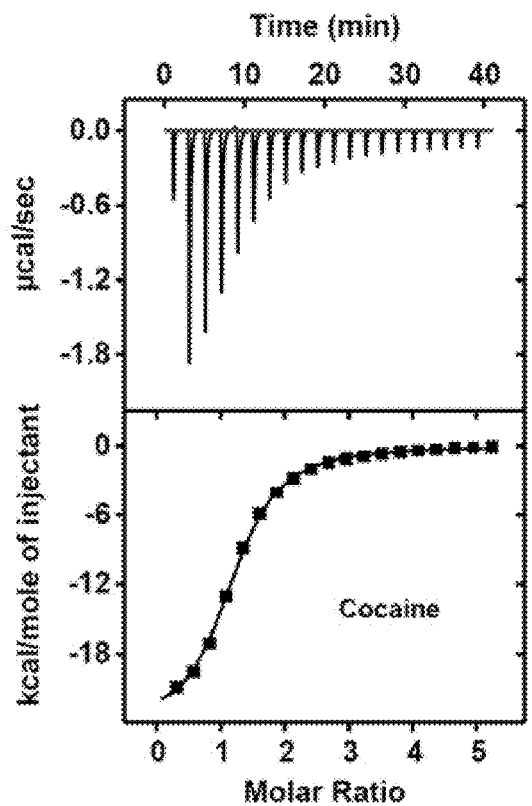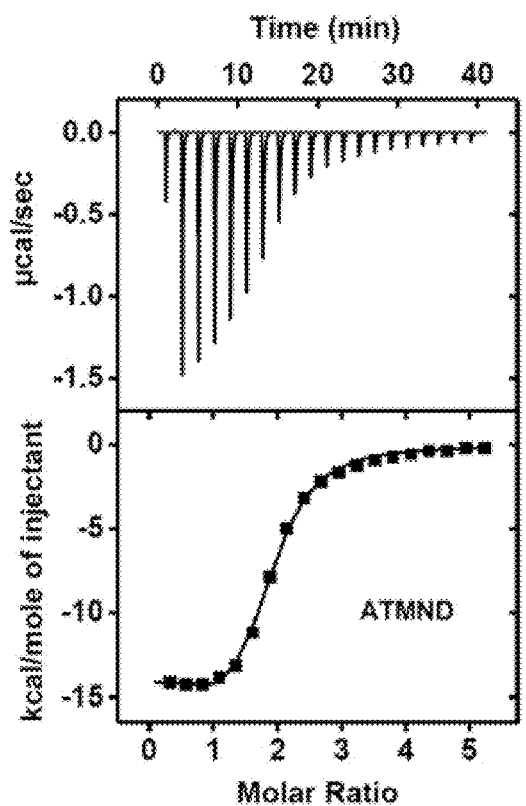
FIG. 5A  FIG. 5B
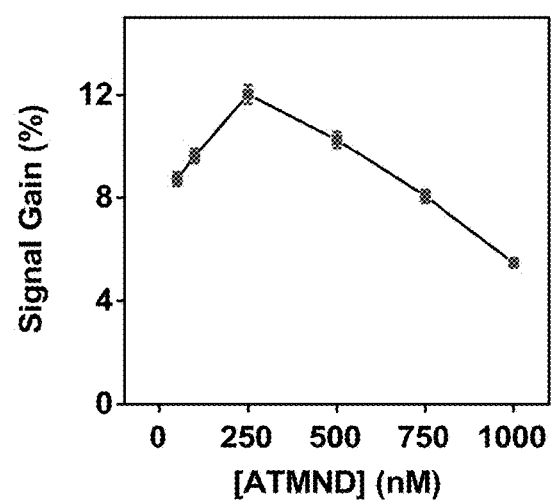
FIG. 6

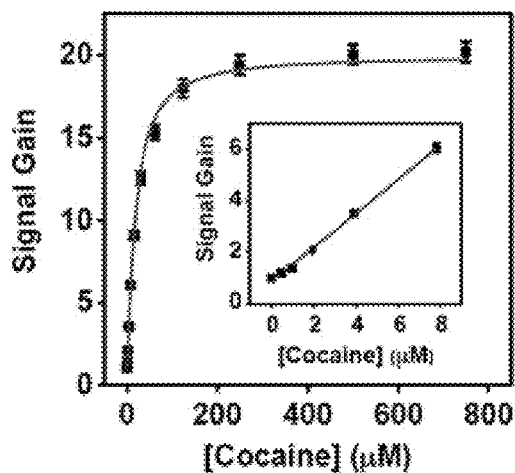
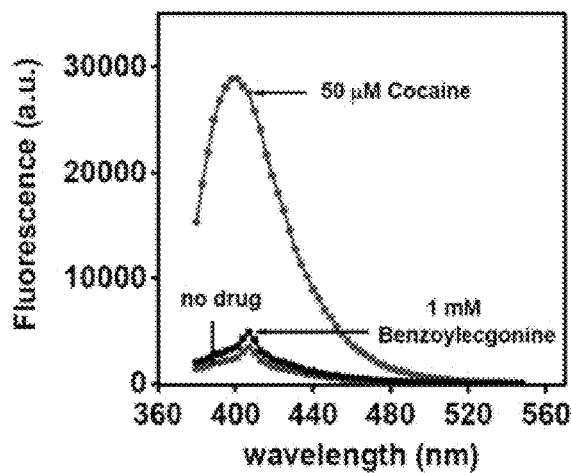
FIG. 7A
FIG. 7B
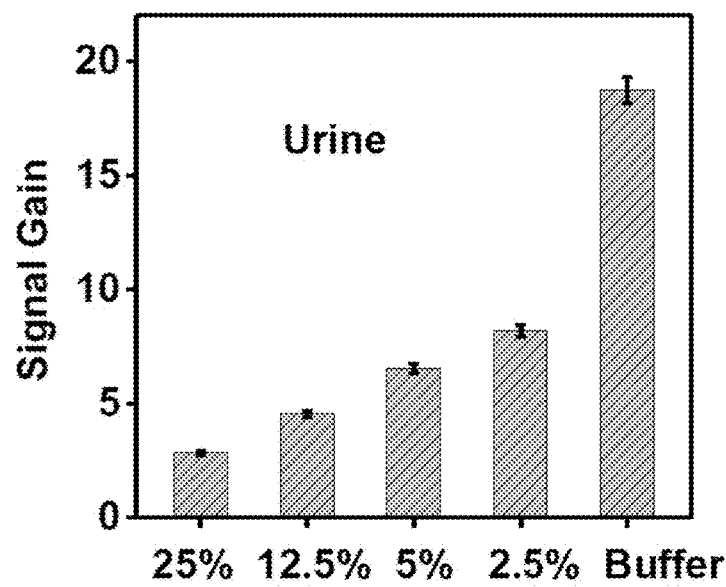
FIG. 8

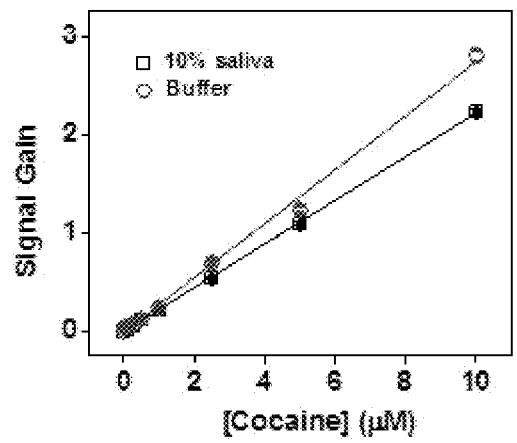 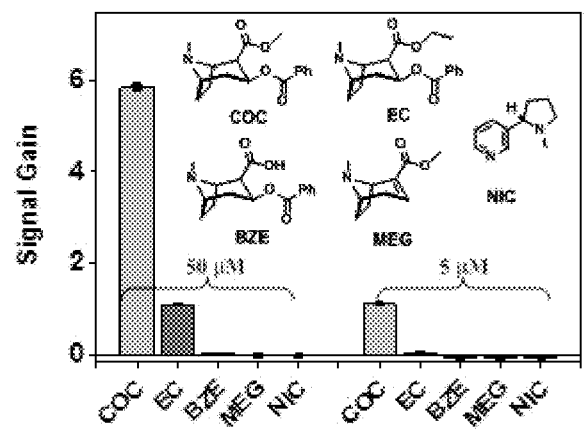
FIG. 19A          FIG. 19B
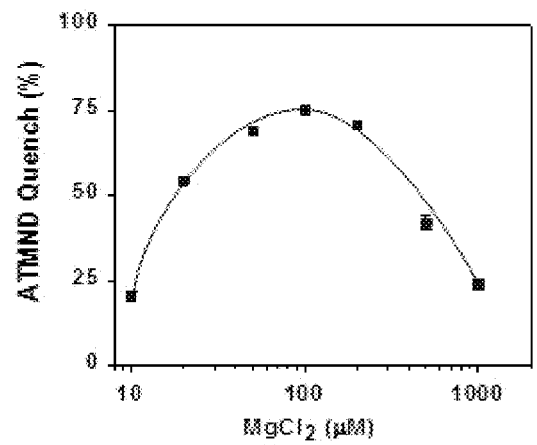 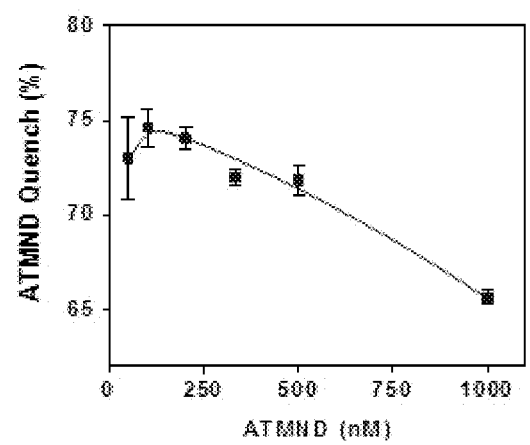
FIG. 20A          FIG. 20B

MATERIALS AND METHODS FOR RAPID AND SPECIFIC DETECTION OF COCAINE

CROSS-REFERENCE TO A RELATED APPLICATION

This application claims the benefit of U.S. Provisional Application Ser. No. 62/073,718, filed Oct. 31, 2014, which is incorporated herein by reference in its entirety.

GOVERNMENT SUPPORT

The subject invention was made with government support under a research project supported by National Institute of Justice under Grant No. 2013-DN-BX-K032. The government has certain rights in this invention.

The Sequence Listing for this application is labeled "SeqList-11Jan16-ST25.txt", which was created on Jan. 11, 2016, and is 8 KB. The entire content is incorporated herein by reference in its entirety.

BACKGROUND OF INVENTION

Cocaine is a central nervous system stimulant that increases levels of dopamine and potently inhibits neurotransmitter reuptake at the synapse. Abuse of cocaine has been shown to cause anxiety, paranoia, mood disturbances, organ damage, and violent behavior. Therefore, rapid detection of cocaine is needed to confirm suspicion of recent use in impaired driver investigations or to assist in overdose treatment in medical emergency settings.

Various immunoassays have been developed for the detection of cocaine and/or its major metabolite benzoylecgonine in biofluids, including the enzyme-linked immunosorbent assay (ELISA) and the EMIT II Plus Cocaine Metabolite Assay. Unfortunately, the use of these assays is often limited because of the high cost of generating antibodies and issues with poor specificity. These antibody-based tests often cannot distinguish between the targeted drug and structurally similar substances, resulting in cross reactivity-related false positives.

Aptamers are single-stranded RNA or DNA molecules selected in vitro via Systematic Evolution of Ligands by Exponential Enrichment (SELEX) (Tuerk, C.; Gold, L. *Science.* 1990, 249, 505-510) to specifically bind to targets with high affinity, and they offer a practical alternative to antibodies for the detection of nucleic acids, proteins and small molecules. Compared to antibodies, aptamers are relatively fast and cheap to produce, and can be chemically synthesized with extreme accuracy and reproducibility. In aptamers having a three-way junction structure the intact stem 3 is essential for cocaine binding, while stem 1 and stem 2 both contribute to the stability of the target-induced three-way junction structure (D. Roncancio, H. Yu, X. Xu, S. Wu, R. Liu, J. Debord, X. Lou, Y. Xiao, *Anal. Chem.* 2014, 86, 11100-6). Due to the high stability of DNA aptamers, they can be stored and used under harsher conditions, and can achieve a longer shelf life (W. Mok, Y. Li, *Sensors* 2008, 8, 7050-7084). It is possible to generate unstructured aptamers that form specific secondary structures such as three-way junctions (M. N. Stojanovic, P. de Prada, D. W. Landry, *J. Am. Chem. Soc.* 2001, 123, 4928-31; K.-A. Yang, M. Barbu, M. Halim, P. Pallavi, B. Kim, D. M. Kolpashchikov, S. Pecic, S. Taylor, T. S. Worgall, M. N. Stojanovic, Nat. Chem. 2014, 6, 1003-8) or G-quadruplexes (L. C. Bock, L. C. Griffin, J. A. Latham, E. H. Vermaas, J. J. Toole, Nature 1992, 355, 564-6; D. E. Huizenga, J. W. Szostak, Biochemistry 1995, 34, 656-665) upon target binding. Such target-induced conformational changes can be readily exploited for specific target detection in a variety of applications including medical diagnostics, environment monitoring and drug screening (T. Mairal, V. C. Ozalp, P. Lozano Sánchez, M. Mir, I. Katakis, C. K. O'Sullivan, Anal. Bioanal. Chem. 2008, 390, 989-1007; J. H. Lee, M. V Yigit, D. Mazumdar, Y. Lu, Adv. Drug Deliv. Rev. 2010, 62, 592-605; E. J. Cho, J.-W. Lee, A. D. Ellington, Annu. Rev. Anal. Chem. (Palo Alto. Calif.). 2009, 2, 241-64). Aptamer-based sensors have gained popularity because of their simplicity and specificity. For example, derivatives of the MNS-4.1 cocaine-binding aptamer (Stojanovic, M. N.; Prada, P.; Landry, D. W. *J. Am. Chem. Soc.* 2000, 122, 11547-11548) have been labeled with sensing elements such as fluorophore/quencher pairs (Stojanovic, M. N.; Prada, P.; Landry, D. W. *J. Am. Chem. Soc.* 2001, 123, 4928-4931); magnetic or metallic nanoparticles (Du, Y.; Li, B.; Guo, S.; Zhou, Z.; Zhou, M.; Wang, E.; Dong, S. *Analyst* 2011, 136, 493-497; Zhang, J.; Wang, L.; Pan, D.; Song, S.; Boey, F. Y. C.; Zhang, H.; Fan, C. *Small* 2008, 4, 1196-1200; Liu, J.; Lu, Y. *Angew. Chem. Int. Ed* 2006, 45, 90-94), quantum dots (Zhang, C. Y.; Johnson, L. W. *Anal. Chem.* 2009, 81, 3051-3055; Liu, J.; Lee, J. H.; Lu, Y. *Anal. Chem.* 2007, 79, 4120-4125) and methylene blue (Baker, B. R.; Lai, R. Y.; Wood, M. S.; Doctor, E. H.; Heeger, A. J.; Plaxco, K. W. *J. Am. Chem. Soc.* 2006, 128, 3138-3139; Swensen, J. S.; Xiao, Y.; Ferguson, B. S.; Lubin, A. A.; Lai, R. Y.; Heeger, A. J.; Plaxco, K. W.; Soh, H. T. *J. Am. Chem. Soc.* 2009, 131, 4262-4266) to achieve specific detection of cocaine.

In the absence of cocaine, the aptamer population exists in an equilibrium state consisting of both folded and unfolded structures (Neves, M. A.; Reinstein, O.; Johnson, P. E. *Biochemistry* 2010, 49, 8478-8487), where the folded structures generate a background signal. When challenged with cocaine, the unfolded aptamers undergo a target-induced conformational change and form a non-canonical three-way junction that binds cocaine, producing a signal change. This limited target-induced fluorescence change results in a high detection limit (10 μM) even under optimal conditions, and the reason may be due to inefficient proximity quenching, low aptamer target binding affinity, or both (Stojanovic, M. N.; Prada, P.; Landry, D. W. *J. Am. Chem. Soc.* 2001, 123, 4928-4931). In addition, target-induced conformational changes are hard to control, especially for small-molecule-binding aptamers that have relatively high (~μM) dissociation constants (KD) (M. McKeague, M. C. Derosa, J. Nucleic Acids 2012, 2012, DOI 10.1155/2012/748913).

Different strategies such as target-displacement have been used to increase the sensitivity of aptamer-based detection. For example, Stojanovic's group used unmodified MNS-4.1 (FIG. 1A, MNS-4.1) to construct a colorimetric cocaine sensor based on cocaine-mediated displacement of a cyanine dye (diethylthiotricarbocyanine iodide; Cy7) from the dye-aptamer complex (Stojanovic, M. N.; Landry, D. W. *J. Am. Chem. Soc.* 2002, 124, 9678-9679). They observed decreased absorbance of Cy7 at 760 nm with increasing cocaine concentrations in the range of 2 to 600 μM and increased sensitivity compared to the corresponding fluorescence sensor due to the high binding affinity of unmodified MNS-4.1 aptamer for cocaine. However, the MNS-4.1 aptamer formed a three-way junction even before binding cocaine (M. N. Stojanovic, D. W. Landry, J. Am. Chem. Soc. 2002, 124, 9678-9) leading to high background signal. In order to achieve a target-induced conformational change, Stojanovic et al. had truncated the sequence to destabilize the aptamer so that it remained unstructured in the absence of cocaine (M. N. Stojanovic, P. de Prada, D. W. Landry, J. Am. Chem. Soc. 2001, 123, 4928-31). This aptamer underwent cocaine-induced folding, but still exhibited some folding activity in the absence of target, resulting in a high background signal that significantly limited sensor sensitivity (M. N. Stojanovic, P. de Prada, D. W. Landry, J. Am. Chem. Soc. 2001, 123, 4928-31; B. R. Baker, R. Y. Lai, M. S. Wood, E. H. Doctor, A. J. Heeger, K. W. Plaxco, J. Am. Chem. Soc. 2006, 128, 3138-9). Subsequently, sensor background was reduced by splitting MNS-4.1 into two or three fragments (M. N. Stojanovic, D. W. Landry, P. de Prada, J. Am. Chem. Soc. 2000, 122, 11547-11548; R. Zou, X. Lou, H. Ou, Y. Zhang, W. Wang, M. Yuan, M. Guan, Z. Luo, Y. Liu, RSC Adv. 2012, 2, 4636-4638). This splitting greatly destabilized the aptamer such that the fragments were unable to assemble in the absence of the target, resulting in a minimal background signal, while retaining the capacity of the fragments for target recognition and reassembly into a complex tertiary structure in the presence of cocaine. However, the aptamer splitting notably interfered with target binding, resulting in reduced target affinity.

In specific embodiments, the subject invention provides split aptamer sensors that have more than one ligand-binding site. Cooperative binding behavior is commonly observed in ligand-binding proteins that are highly sensitive to ligand concentration, such as hemoglobin (W. A. Eaton, E. R. Henry, J. Hofrichter, A. Mozzarelli, Nat. Struct. Biol. 1999, 6, 351-8), ion channels (T. Meyer, D. Holowka, L. Stryer, Science, 1988, 240, 653-656), and transcription factors (T. Krell, W. Terán, O. L. Mayorga, G. Rivas, M. Jiménez, C. Daniels, A.-J. Molina-Henares, M. Martinez-Bueno, M.-T. Gallegos, J.-L. Ramos, J. Mol. Biol. 2007, 369, 1188-99). Those proteins generally have more than one ligand-binding site, where binding at one site increases the affinity of the other sites. As a result, ligand sensitivity can be greatly increased by cooperative binding, showing a 'switch-like' binding curve (D. Bray, Nature 1995, 376, 307-12).

BRIEF SUMMARY

The subject invention provides rapid and specific aptamer-based methods for detection of cocaine and other small molecules. Specifically, exemplified herein is a method for detecting cocaine in bodily fluids and drinks. The subject invention is based on an aptamer sensor that reports the presence of cocaine via the displacement and unquenching of a bound fluorophore molecule.

In a preferred embodiment, the subject invention provides a novel aptamer that has high affinity for both a fluorophore, as well as for cocaine, wherein binding of cocaine to the aptamer causes the fluorophore to be rapidly displaced from the aptamer, even when cocaine is present in low concentrations. In a preferred embodiment, the fluorescent molecule is 2-amino-5,6,7-trimethyl-1,8-naphthyridine (ATMND) which binds the aptamer to quench its fluorescence.

Thus, in a preferred embodiment, the subject invention utilizes cocaine-mediated displacement, employing an aptamer sensor that reports the presence of cocaine via the displacement and unquenching of a bound fluorophore molecule. Because this aptamer also binds cocaine, the competitive binding of cocaine results in a rapid displacement of the ATMND from the aptamer. The released ATMND generates a high-intensity fluorescent signal, reporting the cocaine-binding event.

Advantageously, in accordance with the subject invention, sequence changes have been introduced into the aptamer to create a new cocaine-binding aptamer (38-GC) that exhibits high affinity to both ligands (cocaine and ATMND), while reducing background signal and increasing signal gain.

Using this 38-GC aptamer, a new sensor platform has been developed that relies on the displacement of ATMND from the aptamer by cocaine as a result of competitive binding.

Advantageously, a sensor based on the subject technology can detect cocaine within seconds at concentrations of 200 nM or lower, which is 50-fold lower than the assays based on target-induced conformational change. Also, the assay performs successful cocaine detection in bodily fluids, including saliva, urine and serum samples as well as in drinks.

Therefore, the materials and methods of the subject invention can be used to rapidly detect the presence of cocaine in biological samples, such as urine, saliva, serum and drinks, with high specificity.

The technique of the subject invention makes it possible to derive similar target-dye displacement sensors that also exhibit high specificity and affinity for other small molecules. This approach, therefore, offers a general aptamer-based framework for sensitive, specific and high-throughput on-site drug testing.

In another preferred embodiment, the subject invention provides split-aptamer sensors by incorporating two target-binding domains into a cocaine-specific cooperative-binding split aptamer (CBSA), where the initial cocaine-binding event stabilizes the structure of the split aptamer and assists subsequent target binding in the secondary binding domain. The cooperative behavior of the CBSA of the subject invention results in greater target affinity that considerably increases the extent of target-induced aptamer assembly.

BRIEF DESCRIPTION OF THE FIGURES

FIGS. 1A-1C show structures of the MNS-4.1 (SEQ ID NO:1), 38-GT and 38-GC (SEQ ID NO:2) aptamers.

FIGS. 2A-2D show the scheme of cocaine detection with the 38-GC (SEQ ID NO:2) aptamer sensor.

FIG. 3A shows the time course of ATMND release. In the presence of cocaine, the release of ATMND results in a strong fluorescent signal. FIG. 3B shows the impact of aptamer stability on signaling performance. The signal gain observed in the presence of cocaine was dependent on the composition of stem 1 and stem 3, which contributes to aptamer stability and ATMND/cocaine binding. Experimental conditions: [DNA]=2 µM, [ATMND]=250 nM, [cocaine]=50 µM. Error bars represent the standard deviation of three measurements.

FIGS. 4A-4D show the ITC data demonstrated that MNS-4.1 and 38-GT bind both cocaine and ATMND. ITC data showing heat generated from each injection of (A) cocaine or (B) ATMND into the MNS-4.1 aptamer solution. (C, D) ITC data showing heat generated from each injection and integrated heat plot of (C) cocaine or (D) ATMND into the 38-GT aptamer solution. Experimental conditions: [MNS-4.1 or 38-GT]=20 µM, [ATMND]=500 µM and [cocaine]=500 µM. Binding experiments were performed in 10 mM Tris (pH 7.4) including 0.01 mM $MgCl_2$ and 5% DMSO at 25° C.

FIGS. 5A-5B show the ITC data and integrated heat plots of heat generated from each injection of (A) cocaine or (B) ATMND in the 38-GC solution.

FIG. 6 shows the effect of different concentrations of ATMND on fluorescence signal gain. Maximum signal gain was achieved at an optimized molar ratio between the 38-GC aptamer and ATMND of 8:1. [38-GC]=2 with excitation at 358 nm and emission at 405 nm.

FIGS. 7A-7B show the sensitivity and specificity of the ATMND-based sensor in reaction buffer.

FIG. 8 shows successful detection of cocaine spiked into different dilutions of urine with 38-GC-ATMND. Signal gain decreases with increasing concentrations of urine. Experimental conditions: [38-GC]=2 μM, [ATMND]=250 nM and [cocaine]=500 μM, with excitation at 358 nm and emission at 405 nm. Error bars represent the standard deviation of three measurements.

FIGS. 19A-19B show the validation of the CBSA-based sensor for detecting cocaine in saliva. (A) Calibration curve for the CBSA-5335-based cocaine sensor in buffer and 10% saliva at different cocaine concentrations. (B) Signal gains from the CBSA-5335 sensor in the presence of 50 μM (left) and 5 μM (right) cocaine (COC) or potential interferents including cocaethylene (EC), benzoylecgonine (BZE), anhydroecgonine methyl ester (MEG) and nicotine (NIC). Structures of these various molecules are shown inset. Error bars show the standard deviation of signal gains obtained from three measurements at each concentration.

FIGS. 20A-20B show the optimization of $Mg^{2+}$ and ATMND concentrations for the CBSA-based fluorescence assay. (A) ATMND quenching by target-induced CBSA assembly upon addition of 250 μM cocaine varies at $Mg^{2+}$ concentrations ranging from 10-1000 μM in buffer. (B) ATMND quenching in the presence of 250 μM cocaine also varied at ATMND concentrations ranging from 50-1000 nM in buffer. Quenching was calculated by (F0−F)/F0×100%, where F0 is the fluorescence of the ATMND-CBSA mixture without cocaine and F is the fluorescence of the mixture upon addition of 250 μM cocaine. Error bars show standard deviations obtained from three measurements.

BRIEF DESCRIPTION OF THE SEQUENCES

Figure 4C:
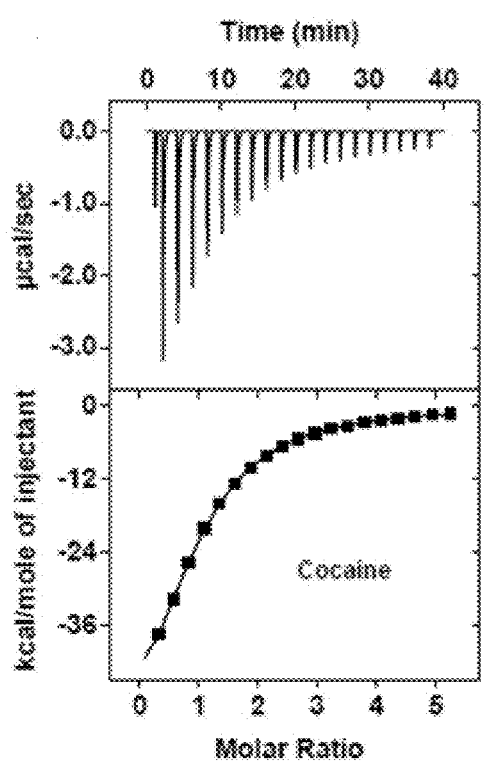

SEQ ID NO: 1 is the nucleic acid sequence of aptamer 38-GT.
SEQ ID NO: 2 is the nucleic acid sequence of aptamer 38-GC.
SEQ ID NO: 3 is the nucleic acid sequence of aptamer 38-GC M1.
SEQ ID NO: 4 is the nucleic acid sequence of aptamer 38-GC M2.
SEQ ID NO: 5 is the nucleic acid sequence of aptamer MNS-4.1.
SEQ ID NO: 6 is the nucleic acid sequence of the long fragment of CBSA-5325.
SEQ ID NO: 7 is the nucleic acid sequence of the short fragment of CBSA-5325, wherein iSpC3 represents internal C3 spacer.
SEQ ID NO: 8 is the nucleic acid sequence of the short fragment of CBSA-5325-Cy5, wherein 5IAbRQ represents Iowa Black RQ, iSpC3 represents internal C3 spacer, and 3Cy5Sp represents Cy5.
SEQ ID NO: 9 is the nucleic acid sequence of the long fragment of CBSA-5335.
SEQ ID NO: 10 is the nucleic acid sequence of the short fragment of CBSA-5335, wherein iSpC3 represents internal C3 spacer.
SEQ ID NO: 11 is the nucleic acid sequence of the short fragment of CBSA-5335-Cye5, wherein 5IAbRQ represents Iowa Black RQ, iSpC3 represents internal C3 spacer, and 3Cy5Sp represents Cy5.
SEQ ID NO: 12 is the nucleic acid sequence of the long fragment of CBSA-5334.
SEQ ID NO: 13 is the nucleic acid sequence of the short fragment of CBSA-5334, wherein iSpC3 represents internal C3 spacer.
SEQ ID NO: 14 is the nucleic acid sequence of the long fragment of CBSA-6225.
SEQ ID NO: 15 is the nucleic acid sequence of the short fragment of CBSA-6225, wherein iSpC3 represents internal C3 spacer.
SEQ ID NO: 16 is the nucleic acid sequence of the long fragment of CBSA-4425.
SEQ ID NO: 17 is the nucleic acid sequence of the short fragment of CBSA-4425, wherein iSpC3 represents internal C3 spacer.
SEQ ID NO: 18 is the nucleic acid sequence of the long fragment of CBSA-LSA.
SEQ ID NO: 19 is the nucleic acid sequence of the long fragment of CBSA-SSA.
SEQ ID NO: 20 is the nucleic acid sequence of the short fragment of CBSA-SSA, wherein iSpC3 represents internal C3 spacer.
SEQ ID NO: 21 is the nucleic acid sequence of the long fragment of CBSA-M1.
SEQ ID NO: 22 is the nucleic acid sequence of the long fragment of CBSA-M2.
SEQ ID NO: 23 is the nucleic acid sequence of aptamer 38-GC-20A.
SEQ ID NO: 24 is the nucleic acid sequence of aptamer 38-GC-20C.
SEQ ID NO: 25 is the nucleic acid sequence of aptamer 38-GC-21T.
SEQ ID NO: 26 is the nucleic acid sequence of aptamer 38-GC-22T.
SEQ ID NO: 27 is the nucleic acid sequence of aptamer 38-GC-22G.
SEQ ID NO: 28 is the nucleic acid sequence of the long fragment of CBSA.
SEQ ID NO:29 is the nucleic acid sequence of the short fragment of CBSA.

DETAILED DISCLOSURE

The subject invention provides a rapid and specific aptamer-based method for one-step cocaine detection. In a specific embodiment, the cocaine-binding aptamer of the subject invention binds the fluorescent molecule 2-amino-5,6,7-trimethyl-1,8-naphthyridine (ATMND) and thereby quenches its fluorescence. In the absence of ligand, the cocaine binding aptamer forms three helical stems around a three-way junction. ATMND binds the aptamer at this junction, which results in the quenching of its fluorescence. The aptamer of the subject invention further binds cocaine thereby triggering a conformational rearrangement in the aptamer and the competitive binding of cocaine results in a rapid displacement of ATMND from the aptamer. The released ATMND generates a high-intensity fluorescent signal, reporting the cocaine-binding event.

In one embodiment, the subject invention provides a method for detecting cocaine in a biological sample wherein said method comprises contacting said sample with an aptamer to which ATMND is bound and determining whether an increase in fluorescence occurs, wherein an increase in fluorescence is indicative of the presence of cocaine in the sample.

In a specific embodiment, the subject invention provides a novel aptamer designated 38-GC. The 38-GC aptamer of the subject invention is derived from the previously-reported MNS-4.1 aptamer and incorporates additional complementary base pairs at multiple sites that stabilize aptamer folding, thereby increasing binding affinity to both ligands and reducing background fluorescence.

In another specific embodiment, a novel 38-GT aptamer is provided that is based on the MNS4.1 aptamer but has three putative non-canonical base-pairs in stem 1 converted to Watson-Crick base-pairs, forming a seven-base-pair stem. The 38-GT aptamer provides reduced background fluorescence, tightly bound ATMND, and an increased signal gain in the presence of cocaine.

In a further specific embodiment, the G-T wobble pair in stem 3 of 38-GT is converted to a matched G-C base-pair, which increases structural stability, leads to a further increase of ATMND quenching efficiency and an improved signal gain of 17 with 50 μM cocaine. The greatly enhanced stability of 38-GC likely contributes to its high affinity towards both ligands, favoring formation of stable aptamer-ligand complexes and resulting in low background and high target-displaced signal gain.

In one embodiment, at least 95% of the fluorescence of the ATMND is quenched in an absence of cocaine. In another embodiment, the equilibrium dissociation constant for binding to cocaine is 5.0 μM or less.

The subject invention thus provides a new sensor platform that relies on the cocaine-mediated displacement of ATMND from 38-GC as a result of competitive binding. The 38-GC aptamer of the subject invention has the G-T wobble pair in stem 3 of 38-GT reverted to a matched G-C base-pair, which leads to increased structural stability and a further increase of ATMND quenching efficiency and an improved signal gain with cocaine.

ATMND fluorescence is significantly quenched upon binding to 38-GC; however, ATMND is displaced from the dye-aptamer complex in the presence of cocaine, generating an intense fluorescence signal. The competitive binding of the two ligands to the 38-GC of the subject invention is sequence-specific as demonstrated by targeted mutagenesis.

The assay of the subject invention is remarkably simple, fast and specific. Advantageously, the detection can be performed in a single tube containing the aptamer-ATMND complex and the sample of interest. The assay of the subject invention can be label-free and detection only requires 20 seconds or less at room temperature to achieve a linear range of 0-8 μM with a LOD of 200 nM in buffer, which is about 50-fold lower than assays based on target-induced conformational change.

In preferred embodiments, the assay of the subject invention can achieve successful cocaine detection in body fluids. In specific embodiments, the assay of the subject invention was found to achieve successful cocaine detection in body fluids, with a limit of detection of 10.4 μM, 18.4 μM and 36 μM in undiluted saliva, urine and serum samples, respectively.

In a preferred embodiment, the subject invention provides an optimized molar ratio for 38-GC aptamer and ATMND of 8:1 when 2 μM 38-GC is used, under which a molar ratio of 99.3% dye-aptamer complexes contain only one ATMND molecule bound at the strong binding site, while the concentration of complexes containing two ATMND molecules is sufficiently low as to be negligible.

Advantageously, the subject invention provides a sensor that specifically responds to cocaine but exhibits almost no response to closely related molecules.

The subject invention provides for target-ligand displacement sensors based on the well-established SELEX technique, which sensors can also exhibit high specificity and affinity for other small molecules. Thus, in further embodiments, the subject invention provides a general framework for performing rapid and specific high-throughput on-site drug testing.

In a specific preferred embodiment, the subject invention provides novel cooperative binding split aptamer (CBSA) sensors that retain high target affinity by incorporating two target-binding domains. "Cooperative binding" means that binding of cocaine to a first cocaine-binding domain stabilizes the structure of the split aptamer and assists subsequent target-binding in the secondary binding domain. The cooperative behavior of the CBSA results in greater target affinity that considerably increases the extent of target-induced aptamer assembly compared to the split aptamers with a single binding domain.

Advantageously, the CBSA-based sensors of the subject invention are able to detect cocaine within 10 minutes at concentrations as low as 25 nM, which is 400-fold lower than single-domain, split aptamer-based sensors. In preferred embodiments, the subject invention provides CBSA-based assays that achieve sensitive and reproducible cocaine detection in saliva samples, with a limit of detection of 50 nM cocaine within 10 minutes at room temperature in 10% diluted saliva and of 500 nM in undiluted saliva. Advantageously, the assay of the subject invention can be used as an on-site testing assay.

In further embodiments, CBSA-based sensors are provided that are developed from either existing aptamers or new aptamers isolated via SELEX for other drugs of abuse as well as clinically relevant targets such as small-molecule biomarkers, toxins, and therapeutics.

In some embodiments, the CBSA-based sensor of the subject invention is integrated into different optical and electrochemical sensing platforms for various on-site applications.

In further embodiments, the performance of the CBSA-based sensor of the subject invention is employed with signal amplification techniques.

In specific embodiments, the CBSA-based sensors of the subject invention have a short fragment and a long fragment, which form two tandem cocaine-binding domains when fully assembled by the target. Advantageously, in the absence of target, the fragments of the CBSA-based sensor remain separated, leading to low background signal.

In a preferred embodiment, the CBSA sensors of the subject invention contain a C3 spacer inserted as an apurinic (AP) site between the two binding domains of the short fragment and a thymidine at the opposite position in the long fragment. Advantageously, when cocaine is present and the short and long fragment of CBSA assemble, ATMND strongly binds to the T nucleotide-containing duplexed AP site of the CBSA of the subject invention, leading to quenching of the ATMND fluorescence. In preferred embodiments, the CBSA of the subject invention is CBSA-5325.

In one embodiment, the subject invention provides a method using Isothermal Titration calorimetry (ITC) to evaluate target binding affinity and responsiveness of aptamers to target-induced assembly. Advantageously, the equilibrium dissociation constants of the first and second cocaine-binding domains of CBSA-5325 are 283 µM and 106 µM, confirming cooperative binding behavior.

In a further embodiment, at least 76% of the fluorescence of the ATMND is quenched within 10 minutes of cocaine being present. In a preferred embodiment, the ATMND concentration is 200 nM. In another preferred embodiment, the $Mg^{2+}$ concentration is 100 In a further embodiment, the equilibrium dissociation constant for ATMND binding to CSBA is 365 nM.

In another preferred embodiment, the subject invention provides a method for detecting cocaine in a biological sample, wherein said method comprises contacting said sample with a short and a long fragment of a CBSA aptamer and free ATMND molecules, wherein the short and long fragments remain separated in the absence of cocaine and the free ATMND molecules generate strong fluorescence, wherein a decrease in fluorescence occurs when cocaine is present and the decrease in fluorescence is indicative of the amount of cocaine present in the sample.

The subject invention further provides methods to characterize substrate binding mechanisms and affinities. In one embodiment, the subject invention provides split aptamers with truncated substrate binding domains. In one specific embodiment, the subject invention provides a short split aptamer with only a single target binding domain. In another specific embodiment, the subject invention provides a long split aptamer with only a single target binding domain. In a further specific embodiment, the subject invention provides CBSAs in which either of the two target binding domains is disrupted by a single-nucleotide mutation.

In another embodiment, the subject invention provides mutated derivatives of 38-GC. For example, in one embodiment, an adenosine at position 22 in 38-GC is replaced with a guanine (38-GC-22G), wherein the mutation is located in the long fragment at the 3' binding domain (CBSA-M1). In another embodiment, the replacement of guanine at position 22 in 38-GC with adenosine is placed in the long fragment at the 5' binding domain (CBSA-M2). In preferred embodiments, the CBSA of the subject invention is not modified relative to the split 38-GC-based CBSA at position 22 in the long fragment at the 3' binding domain or the 5' binding domain, respectively.

In a preferred embodiment, the subject invention provides CBSAs with a fixed total number of complementary base pairs but an increased number of base pairs between the two target binding domains. In another embodiment, the subject invention provides CBSAs with a fixed total number of complementary base pairs but a decreased number of base pairs between the two target binding domains.

In a preferred embodiment, the subject invention provides CBSAs with an increased total number of base pairs wherein an A-T base pair has been added into segment C. In a more preferred embodiment, the CBSA with an A-T base pair added into segment C is CBSA-5335. Advantageously, cocaine-induced aptamer assembly in CBSA-5335 is enhanced compared to CBSA-5325, and equilibrium dissociation constants of the cocaine-binding domains of CBSA-5335 are 97.1 µM and 17.5 µM, respectively, which are 2.9- and 6.1-fold lower than the values for CBSA-5325. The CBSA-5335 aptamer of the subject invention is a preferred embodiment for the fabrication of signal-on fluorophore/quencher-modified CBSAs for ultrasensitive cocaine detection in biological fluids including drinks.

In preferred embodiments, the subject invention provides ultra-sensitive signal-on fluorophore/quencher-modified CBSA sensors that contain a fluorophore at one terminus of the short fragment of the CBSA and a quencher at the other end of the short fragment. Advantageously, in the absence of target molecules, the short and long CBSA fragments of the ultra-sensitive CBSA sensor of the subject invention remain separated, bringing the fluorophore in close proximity to the quencher due to the flexibility of the single-stranded short fragment, whereby the quencher quenches fluorescence, which leads to low background signal. In preferred embodiments, in the presence of target molecules, the fluorophore/quencher-modified CBSAs assemble, wherein the long and short fragment associate into rigid aptamer-target structures whereby the quencher and fluorophore separate and the increase in fluorescence is indicative of the amount of target molecules. In preferred embodiments, the quencher at the 5' terminus of the short fragment is an Iowa Black RQ black quencher and the fluorophore at the 3' terminus of the short fragment is a Cy5 fluorophore. Advantageously, the excitation wavelength for Cy5, 648 nm, is incapable of inducing fluorescence in molecules normally found in saliva matrices. Advantageously, the fluorophore/quencher-modified CBSA of the subject invention has a limit of detection for cocaine of 25 nM in buffer and of 50 nM in 10% diluted saliva.

In further embodiments, the fluorophore/quencher-modified CBSA of the subject invention has excellent target specificity and does not give a measurable signal from 500 µM of benzoylecgonine, anhydroecgonine methyl ester or nicotine in undiluted saliva and only 19% and 3% cross-reactivity to 500 µM and 50 µM cocaethylene in undiluted saliva, respectively.

EXAMPLES

Following are examples that illustrate embodiments and procedures for practicing the invention. These examples should not be construed as limiting.

Example 1—Cocaine-Binding Aptamers

To develop a cocaine displacement-based sensor platform, a signal reporter is needed that binds to the cocaine-binding aptamer but can also be displaced by cocaine, reporting the presence of target. ATMND was purchased from Ryan Scientific, and 3,3'-diethylthiatricarbocyanine iodide (Cy7) was purchased from Sigma-Aldrich; any dilution or stock solution was prepared with dimethyl sulfoxide (DMSO). Cocaine hydrochloride was purchased from Sigma-Aldrich and benzoylecgonine tetrahydrate was purchased from Cerilliant Corporation. Both 50 mM stock solutions were prepared in HCl solution (pH 4.5) and stored at 4° C. All DNA aptamers were ordered from Integrated DNA Technologies with HPLC purification, and dissolved to a concentration of 500 µM in 1× filtered TE buffer (10 mM Tris, 1 mM EDTA, pH 8.0). DNA concentrations were measured on a NanoDrop 2000 (Thermo Scientific). DNA sequences are listed below:

```
38-GT:
                                       (SEQ ID NO: 1)
5' GGG AGA CAA GGA AAA TCC TTC AAT GAA
GTG GGT CTC CC 3';

38-GC:
                                       (SEQ ID NO: 2)
5' GGG AGA CAA GGA AAA TCC TTC AAC GAA
GTG GGT CTC CC 3';

38-GC M1:
                                       (SEQ ID NO: 3)
5' GGG AGA CAA GGA AAA TCC TCT AAC GAA
GTG GGT CTC CC 3';

38-GC M2:
                                       (SEQ ID NO: 4)
5' GGG AGA CAA GGA AAA TCC TAC AAC GAA
GTG GGT CTC CC 3';

MNS-4.1:
                                       (SEQ ID NO: 5)
5' GGG AGA CAA GGA TAA ATC CTT CAA TGA
AGT GGG TCG ATA 3'.
```

ATMND Binding and Cocaine Displacement Experiments:

For cocaine detection, we prepared 96 μL of reaction buffer (10 mM Tris, 0.01 mM MgCl$_2$, pH 7.4), 1 μL aptamer (final concentration 2 μM) and 1 μL ATMND (final concentration 0.25 μM) solution. Each 98 μL reaction was loaded into one well of a 96-well plate. Fluorescence readings were taken three minutes apart to determine stability of the signal, with excitation at 358 nm and emission at 405 nm. After the signal stabilized for 15 minutes, a 2 μL cocaine solution (0-2.5 mM) was added to each well using a multichannel pipette while monitoring the fluorescence signal. Samples were prepared in triplicate with average values used to plot the figures.

Detection with Cy7:

The same set of experiments was performed with the same solutions as described above for ATMND, but with 1 (final concentration 7 μM) Cy7 instead of ATMND. The absorbance was recorded at 760 nm.

ITC Experiments:

ITC experiments were performed with a MicroCal iTC200 instrument (GE Healthcare). All measurements were performed in 10 mM Tris buffer (pH 7.4) with 0.01 mM MgCl$_2$ and 5% DMSO. The sample cell contained the aptamer solution, while the titrant was loaded in the syringe. In order to detect tight binding, the aptamer concentration was kept at 20 μM while the titrant (cocaine or ATMND) concentration was 500 μM. For the non-split aptamers, 19 total injections of 2 μL each and a purge injection of 0.4 uL were used. The purge injection was not included in the calculations. Two sets of each experiment with cocaine or ATMND were performed at 25° C. The raw data was averaged and fitted to the two sets of sites and single-site binding models and adjusted for the heat of the titrant.

Detection of Cocaine in Urine, Serum and Saliva Using the Original Aptamers:

Different concentrations of biofluids were obtained by dilution with deionized water. To test the quenching effect of biofluids, ATMND (500 nM) was mixed in 2× reaction buffer (20 mM Tris, 0.02 mM MgCl2, pH 7.4) with an equal volume of biofluids, followed by fluorescence measurements. To test the signal gain of cocaine in different biofluid dilutions, cocaine (500 μM) was spiked into 50%, 25%, 10%, 5% and 0% urine, serum and saliva. These were then mixed with an equal volume of 2× reaction buffer containing ATMND (500 nM) and 38-GC (4 μM), followed by subsequent fluorescence recording.

To perform cocaine detection in biofluids, different cocaine concentrations were spiked into 5% urine, 5% serum or 10% saliva. Equal volumes of cocaine-spiked biofluids and 2× reaction buffer containing ATMND (500 nM) and 38-GC (4 μM) were mixed to read the fluorescence. Unless otherwise indicated, fluorescence measurements were obtained with excitation at 358 nm and emission at 405 nm.

The MNS-4.1 aptamer binds to ATMND and cocaine binding can competitively displace ATMND from the aptamer-dye complex. Free ATMND is highly fluorescent in the buffer, but these dye molecules are rapidly bound by MNS-4.1 upon addition of the aptamer, and ATMND fluorescence was greatly quenched within seconds. When 250 nM ATMND was incubated with 2 μM MNS-4.1, roughly 93% of the fluorophore was quenched, with the remaining 7% contributing to the low level of fluorescence background (FIG. 3A).

The aptamer-ATMND complex is very stable, and no detectable fluorescence change over the course of 1 hour was observed. Sensor performance was characterized in terms of signal gain, which is the ratio of the background-subtracted fluorescence obtained with cocaine relative to that obtained in the absence of cocaine, such that a larger signal gain is indicative of better sensitivity. The addition of cocaine is predicted to trigger a conformational rearrangement in the aptamer, with two adjacent GA base pairs and a dinucleotide bulge (T20 and C21) within the aptamer binding pocket. Upon 50 μM cocaine addition, a competitive target binding to MNS-4.1 was observed resulting in successful displacement of ATMND from the aptamer with a signal gain of 9.6. This fluorescence increase was stable for at least several hours. In contrast, no measurable signal change was observed in the absence of cocaine (FIG. 3A).

The aptamer stability impacted signaling performance (FIG. 3B). The signal gain observed in the presence of cocaine was dependent on the composition of stem 1 and stem 3, which contributes to aptamer stability and ATMND/cocaine binding.

Example 2—Modified Aptamer Having Reduced Background Fluorescence

To test whether a completely folded aptamer could reduce background fluorescence and boost signal gain, the 38-GT aptamer (FIG. 1, 38-GT) was engineered by converting the three putative non-canonical base-pairs in stem 1 to Watson-Crick base-pairs, forming a seven-base-pair stem.

The 38-GT resulted in reduced background fluorescence, with 95% ATMND quenched, indicating that ATMND binds tightly to 38-GT. No loss of cocaine-displaced signal was observed and an increased signal gain of 12 in the presence of 50 μM cocaine was obtained (FIG. 3B).

Example 3—Aptamer 38-GC

To further reduce background signal, the G-T wobble pair in stem 3 of 38-GT was converted to a matched G-C base-pair (FIG. 1, 38-GC). This increased structural stability led to a further increase of ATMND quenching efficiency (97%) and an improved signal gain of 17 (FIG. 3B) with 50 μM cocaine.

The greatly enhanced stability of 38-GC likely contributes to its high affinity towards both ATMND and cocaine, favoring formation of stable aptamer-ligand complexes and resulting in low background and high target-displaced signal gain.

Example 4—Binding of Aptamers to Cocaine and ATMND

Isothermal titration calorimetry (ITC) was used to investigate the binding affinity and thermodynamics of MNS-4.1, 38-GT and 38-GC with regard to both ATMND and cocaine. The results confirmed that the aptamers bind both molecules and that binding in both cases is enthalpically driven and entropically unfavorable. ITC stoichiometry data indicated that each aptamer binds to one cocaine molecule or two ATMND molecules.

Figure 4D:
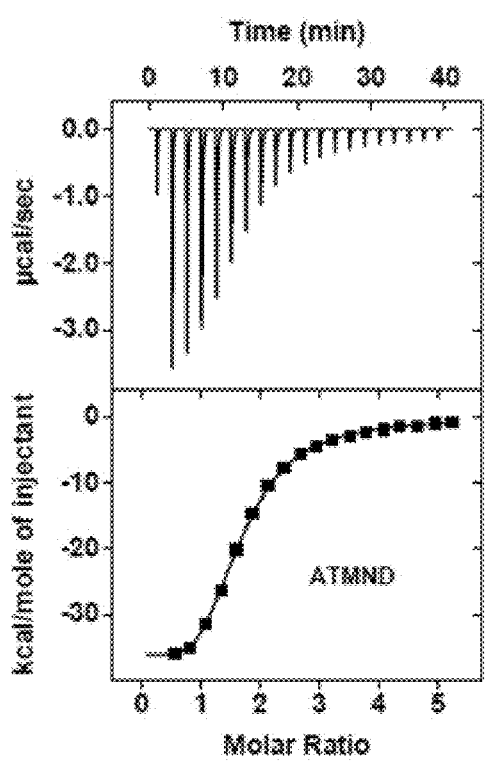

After correction of the dilution heat, the single-site binding model was used to obtain equilibrium dissociation constants ($K_{dc}$) of 6.7±1.3 µM (FIG. 4A), 10±1 µM (FIG. 4C) for cocaine binding to MNS-4.1 and 38-GT, respectively. The two sets of sites binding model was used to obtain affinity measurements for ATMND binding sites on MNS-4.1 ($K_{d1}$, 6.6±0.8 µM; $K_{d2}$, 25±1 µM (FIG. 4C)) and 38-GT ($K_{d1}$, 0.16±0.08 µM; $K_{d2}$, 6.3±1.2 µM (FIG. 4D)). ITC data also showed that the G-C change in 38-GC further increased the stability of the aptamer, leading to increased binding affinity for both ligands. Compared with 38-GT, a 4-fold enhanced binding to cocaine was observed ($K_{dc}$=2.6±1.0 µM) and 10-fold tighter binding to ATMND ($K_{d1}$=0.016±0.001 µM; $K_{d2}$=2.6±1.0 µM) (FIG. 5). 38-GC binds both cocaine and ATMND. (Top) ITC data showing heat generated from each injection of (A) cocaine or (B) ATMND into the 38-GC solution. (Bottom) The integrated heat plot is shown after correcting for the heat of dilution.

These results demonstrate the utility of ATMND as an excellent transduction element; its tight binding to the aptamer results in very low background signal until it becomes displaced via competitive binding of cocaine and recovers its fluorescence.

Example 5—Molar Ratio of Aptamer to ATMND

To minimize the background signal and obtain a high signal-to-noise ratio, a fixed concentration of 38-GC (2 µM) was used to optimize the concentration of ATMND and thus an optimized 38-GC:ATMND ratio of 8:1 was obtained (FIG. 6). Under these conditions, it was calculated that 99.3% dye-aptamer complexes contained only one ATMND molecule bound at the strong binding site, while the concentration of complexes containing two ATMND molecules was sufficiently low as to be negligible.

Example 6—Mechanism of ATMND Binding to the Aptamer

The sensor of the subject invention is based on the premise that both ATMND and cocaine compete for the same aptamer, and that the binding site of both ligands is located within the hydrophobic three-way junction pocket. To confirm this, the extent to which targeted nucleotide changes affect ligand binding and target competition was examined. Mutants of 38-GC were designed in which a nucleotide switch was introduced between T20 and C21 (38-GC-M1) or a replacement of thymine at position 20 with an adenine (38-GC-M2).

These mutant aptamers were tested in a competitive cocaine-binding fluorescence assay. Significantly reduced binding to both ATMND and cocaine, with a high fluorescence background and a low cocaine-displaced fluorescence recovery was noted. This poor ATMND binding and weak cocaine displacement resulted in a signal gain of just 1.3 and 1.2 with 50 µM cocaine for 38-GC-M1 and 38-GC-M2, respectively. This very weak binding affinity of mutant aptamers to both ATMND and cocaine was also confirmed by ITC.

The mutation experiments indicate that ATMND binding is also heavily dependent on C21 and T20. Nakatani et al. (Kobori, A.; Hofie, S.; Suda, H.; Saito, I.; Nakatani, K. *J Am. Chem. Soc.* 2004, 126, 557-562; Suda, H.; Kobori, A.; Zhang, J.; Hayashi, G.; Nakatani, K. *Bioorg. Med. Chem.* 2005, 13, 4507-4512) used $^{15}N$ NMR experiments to reveal that 1,8-naphthridine selectively binds to cytosine or thymine via a three-point hydrogen bond (Rajendar, B.; Sato, Y.; Nishizawa, S.; Teramae, N. *Bioorg. Med. Chem. Lett.* 2007, 17, 3682-3685), and that the binding affinity of ATMND to various target nucleotides is as follows: cytosine>thymine>adenine>guanine (Sato, Y.; Nishizawa, S.; Yoshimoto, K.; Seino, T.; Ichihashi, T.; Morita, K.; Teramae, N. *Nucleic Acids Res.* 2009, 37, 1411-1422). Thus, it is likely that ATMND binds either C21 or T20 within the three-way junction of the aptamer through a three-point hydrogen bond (Zhao, G.-J.; Han, K.-L. *J. Phys. Chem. A* 2007, 111, 9218-9223; Huang, G.-J.; Ho, J.-H.; Prabhakar, C.; Liu, Y.-H.; Peng, S.-M.; Yang, J.-S. *Org. Lett.* 2012, 14, 5034-5037).

Example 7—Sensitivity and LOD

FIG. 7 shows sensitivity and specificity of the ATMND-based sensor in reaction buffer. (A) Calibration curve shows a strong concentration-dependent response to cocaine by 38-GC-ATMND. (B) The aptamer sensor specifically responds to cocaine but exhibits almost no response to its major metabolite benzoylecgonine.

The assay of the subject invention can be performed utilizing a simple, one-pot, one-step reaction that entails simple mixing of 38-GC, ATMND and cocaine at room temperature, and then exploiting the rapid competition between cocaine and ATMND for limited aptamer binding sites to quantitatively detect cocaine in samples. The signal gain increased with cocaine concentration, reaching a saturated signal gain of 19 with 250 µM cocaine (FIG. 7A), with a linear range of 0-8 µM (FIG. 7A, insert). The low background resulting from the high affinity interaction of 38-GC with ATMND yields an excellent limit of detection (LOD). In a reaction with 2 µM 38-GC and 250 nM ATMND, a LOD of 200 nM was achieved within 20 seconds (calculated LOD as S/N>3), more than 50-fold better than most existing aptamer-based systems (Zhang, C. Y.; Johnson, L. W. *Anal. Chem.* 2009, 81, 3051-3055; Swensen, J. S.; Xiao, Y.; Ferguson, B. S.; Lubin, A. A.; Lai, R. Y.; Heeger, A. J.; Plaxco, K. W.; Soh, H. T. *J. Am. Chem. Soc.* 2009, 131, 4262-4266; Qiu, L.; Zhou, H.; Zhu, W.; Jiang, J.; Shen, G.; Yu, R. *New J. Chem.* 2013, 37, 3998-4003), and comparable to sensitive assays that require enzymatic amplification (Table 1).

TABLE 1

Comparison of aptamer-based sensors for cocaine detection

| Method | Limit of detection | Response time |
|---|---|---|
| Cy7 displacement[1], Colorimetric | 2 µM | 12 hours |
| SYBR-gold binding[2], Fluorescence | 5 µM | 3 hours |
| Strand-displacement amplification[3], Fluorescence | 2 nM | >2 hours |
| Aptamer self-assembly[4], Fluorescence | 10 µM | 1-2 hours |
| DNAzyme-amplified detection[5], Colorimetric | 50 nM | 40 min |
| Aptamer conformational change[6], Fluorescence | 2 µM | Minutes |
| Modified gold-nanoparticle[7], Colorimetric | 50 µM | 1 min |
| Microcantilever[8], Interferometric | 5 µM | 25 min |
| Aptamer conformational change[9], Electrochemistry | 10 µM | Seconds |
| 38-GC-ATMND complex, Fluorescence (this work) | 200 nM | Seconds |

The 38-GC-ATMND complex offers a superior signal transduction mechanism for immediate and specific cocaine detection with robust signal gain. Since Cy7 has been used as a signal reporter in previously-reported cocaine-mediated aptamer-based assay (Stojanovic, M. N.; Landry, D. W. *J. Am. Chem. Soc.* 2002, 124, 9678-9679), the sensor performance of 38-GC was compared with either Cy7 or ATMND under optimized conditions, and it was confirmed that 38-GC exhibits much better signal gain and sensitivity with ATMND. For example, the ATMND-based "signal-on" sensor produced an approximate signal gain of 17 with only 1.5% of relative standard deviation (RSD) in the presence of 50 µM cocaine (FIG. 7A), while the same cocaine concentration produced only a 35% signal decrease with 5% of RSD for the Cy7-based "signal-off" sensor.

Example 8—Specificity

The specificity of the assay was tested with benzoylecgonine, which is the corresponding carboxylic acid derivative of cocaine with an otherwise almost identical structure. Relative to the signal gain of 17 obtained with 50 µM cocaine, a measurable signal change was not detected upon addition of 50 µM benzoylecgonine and a signal gain of just 1.7 was observed when the benzoylecgonine concentration was increased to 1 mM (FIG. 7B), which is consistent with the good specificity observed with previous aptamer-based sensors.

Example 9—Detecting Cocaine in Biofluids

The average concentration of cocaine in different body fluids within 24 hours after ingestion is typically greatest in the urine (milligrams per liter), with lower concentrations found in saliva and serum, respectively. The practicality of the CBSA assay for performing cocaine detection in different body fluids collected from healthy donors was explored.

Figure 9:
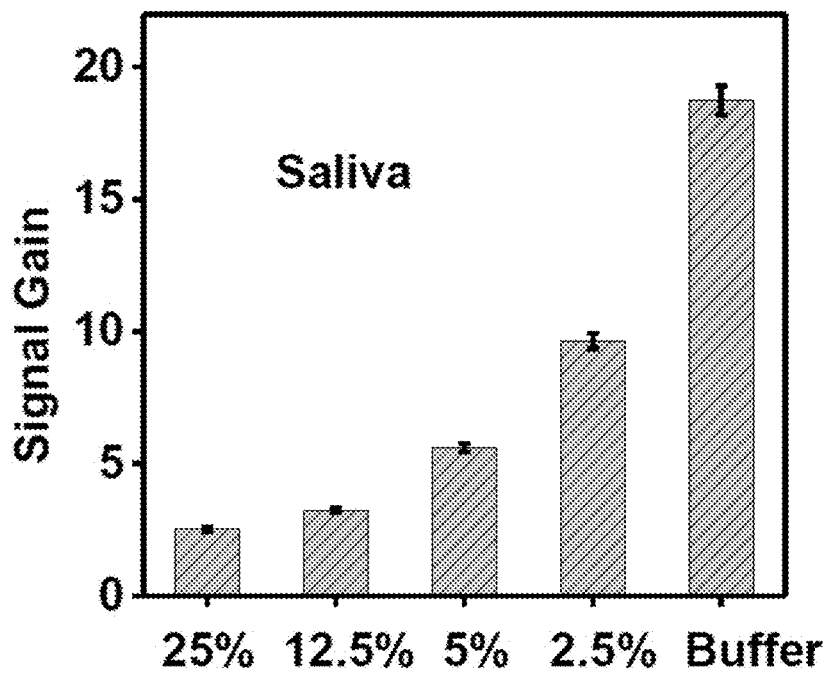
FIG. 9 shows successful detection of cocaine spiked into different dilutions of saliva with 38-GC-ATMND. Signal gain decreases with increasing concentrations of saliva. Experimental conditions: [38-GC]=2 μM, [ATMND]=250 nM and [cocaine]=500 μM, with excitation at 358 nm and emission at 405 nm. Error bars represent the standard deviation of three measurements.
Figure 10:
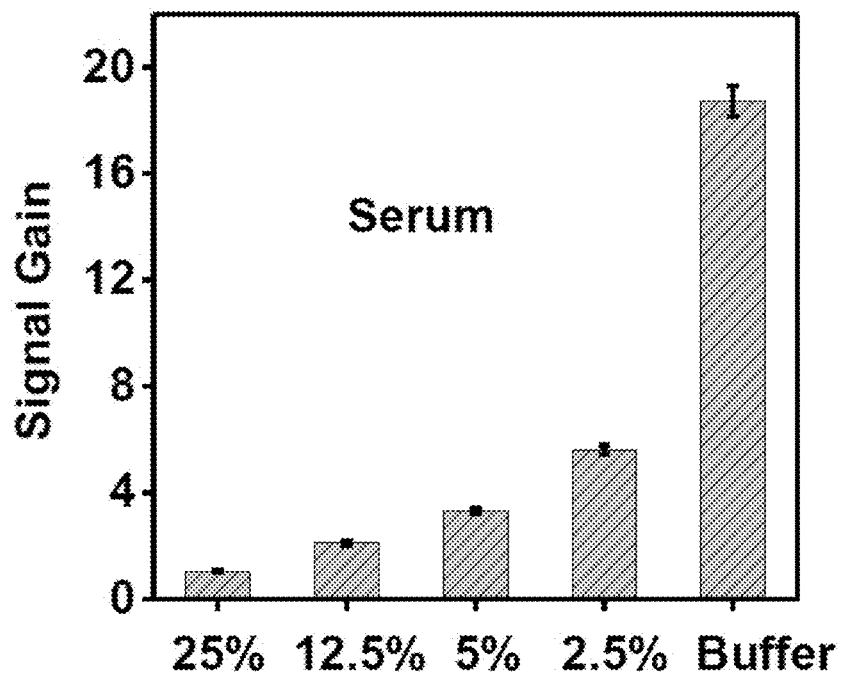
FIG. 10 shows successful detection of cocaine spiked into different concentrations of serum with 38-GC-ATMND. Signal gain decreases with increasing concentrations of serum. Experimental conditions: [38-GC]=2 μM, [ATMND]=250 nM and [cocaine]=500 μM, with excitation at 358 nm and emission at 405 nm. Error bars represent the standard deviation of three measurements.

First, the assay was tested with 250 µM cocaine spiked into various dilutions of urine (FIG. 8), saliva (FIG. 9) or serum (FIG. 10) samples. It was observed that the signal gain increased in inverse proportion to the biofluid concentration, with a maximum signal gain of 8.2, 9.6 and 5.6 for 2.5% urine, saliva and serum, respectively. Human urine normally contains very small amounts of protein (<0.14 mg/mL) and a large number of fluorescent metabolites. It was observed that urine samples indeed generated a strong background fluorescence at 400-550 nm (FIGS. 11 and 12) and metabolites such as pterins, flavins, porphyrins and 4-pyridoxic acid may contribute to this fluorescence. Although the urine matrix exhibited high background fluorescence, it was still possible to achieve successful detection of cocaine. The signal gain increased with increasing cocaine concentrations, with a LOD of 460 nM cocaine in 2.5% urine.

Figure 11:
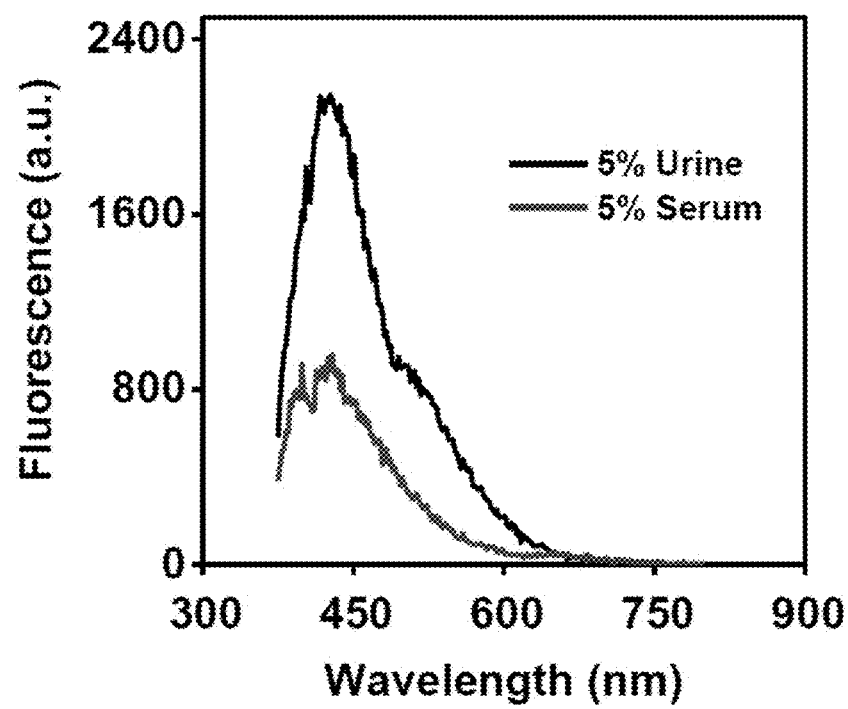
FIG. 11 shows 5% urine and serum samples emit fluorescence within the wavelength range from 375 nm to 600 nm when excited at 358 nm.
Figure 12:
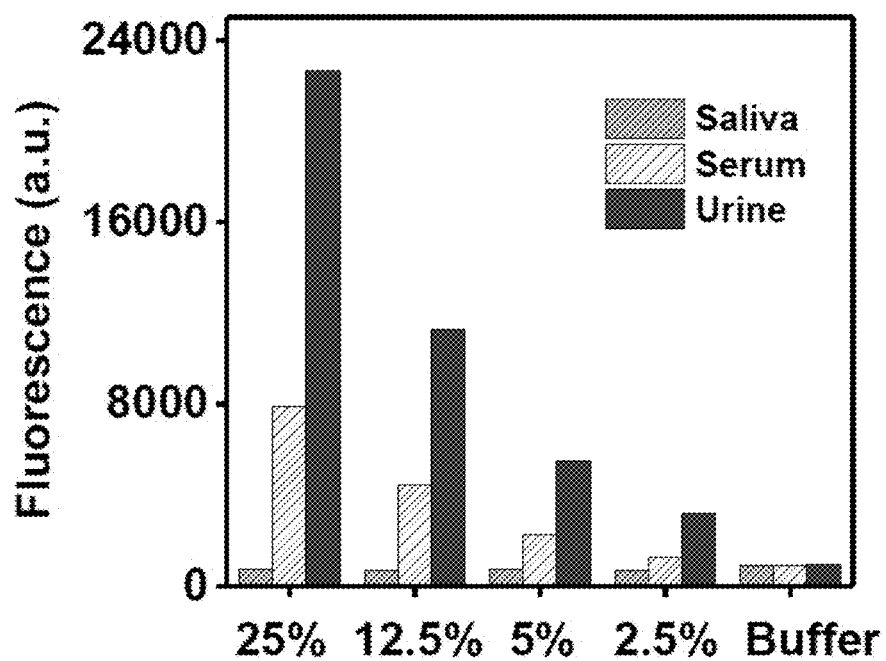
FIG. 12 shows fluorescence intensities for different concentrations of various biofluids. Serum and urine both generate high fluorescence, which increases with the increase of concentration. In contrast, saliva emits no fluorescence. Excitation wavelength: 358 nm, and emission wavelength: 405 nm.
Figure 13:
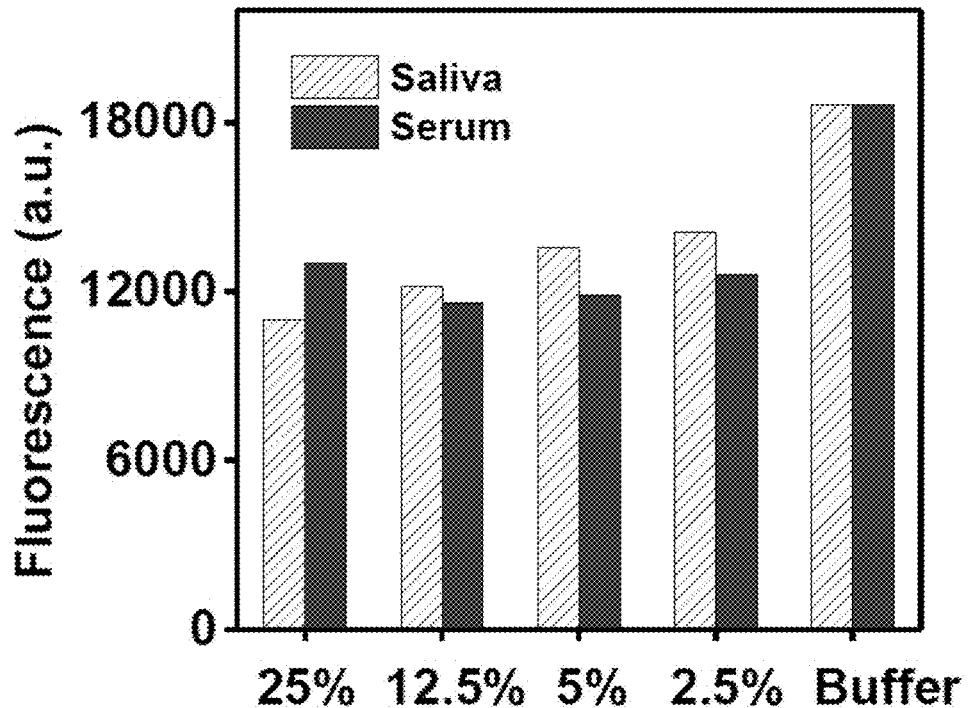
FIG. 13 shows fluorescence intensities of ATMND in different concentrations of saliva and serum. The fluorescence of ATMND was quenched by higher concentrations of saliva and serum. Excitation wavelength: 358 nm, and emission wavelength: 405 nm.

Serum samples generate weak background fluorescence (FIGS. 11 and 12). However, since serum contains ~67 mg/mL protein which might bind ATMND molecules within hydrophobic patches and thereby quench its fluorescence (FIG. 13), these samples were expected to be challenging to work with. Even though serum samples demonstrated considerable ATMND quenching at 405 nm (FIG. 13), it was still possible to detect cocaine in 2.5% serum with a detection limit of 900 nM (FIG. 13). Saliva is a cleaner matrix with no background fluorescence (FIG. 12), containing only 1.6 mg/mL proteins, and it was possible to use 5% saliva to achieve cocaine detection and establish a calibration curve with a LOD of 520 nM. Based on these findings, the detection limits of 10.4 µM, 18.4 µM and 36 µM in undiluted saliva, urine and serum, respectively, were calculated. These experiments successfully demonstrate the utility of using the sensor of the subject invention to detect cocaine in body fluids.

Example 10—Detection of Cocaine in Drinks

Figure 14:
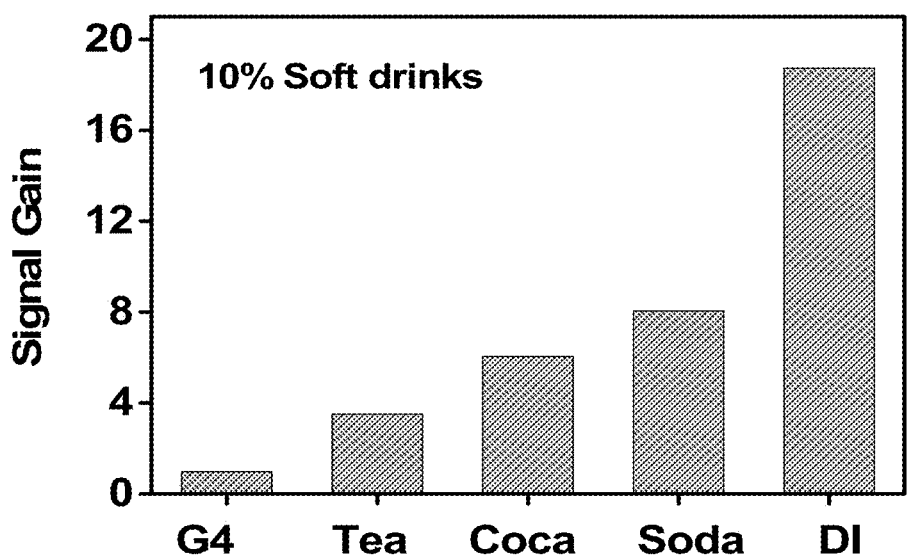
FIG. 14 shows successful detection of cocaine spiked into 10% soft drinks with 38-GC-ATMND. Experimental conditions: [38-GC]=2 μm, [ATMND]=250 nM and [cocaine]=250 μM, with excitation at 358 nm and emission at 405 nm. Error bars represent the standard deviation of three measurements.

FIG. 14 shows successful detection of cocaine spiked into 10% soft drinks with 38-GC-ATMND. Experimental conditions were: [38-GC]=2 µm, [ATMND]=250 nM and [cocaine]=250 µM, with excitation at 358 nm and emission at 405 nm. Error bars represent the standard deviation of three measurements.

Figure 15:
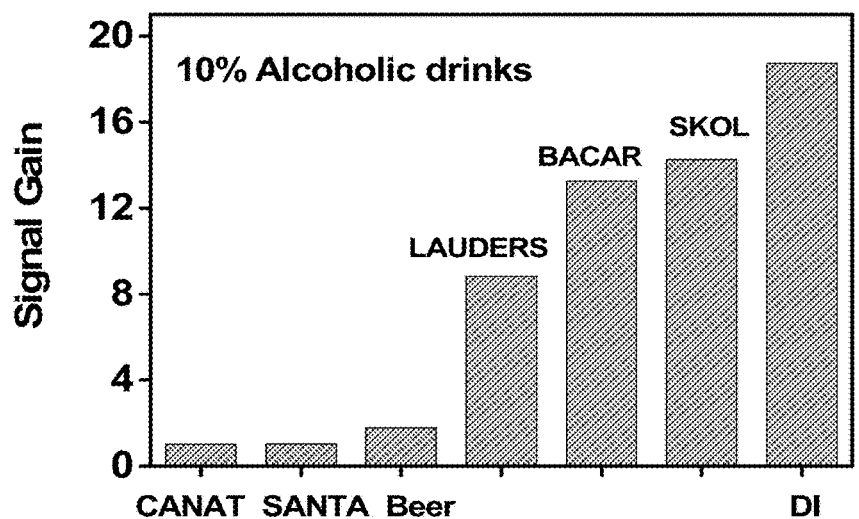
FIG. 15 shows successful detection of cocaine spike into 10% alcoholic drinks with 38-GC-ATMND. Experimental conditions: [38-GC]=2 μM, [ATMND]=250 nM and [cocaine]=250 μM, with excitation at 358 nm and emission at 405 nm. Error bars represent the standard deviation of three measurements.

FIG. 15 shows successful detection of cocaine spike into 10% alcoholic drinks with 38-GC-ATMND. Experimental conditions were: [38-GC]=2 µM, [ATMND]=250 nM and [cocaine]=250 µM, with excitation at 358 nm and emission at 405 nm. Error bars represent the standard deviation of three measurements.

Example 11—Design of Cocaine-Binding CBSAs

Figure 16:
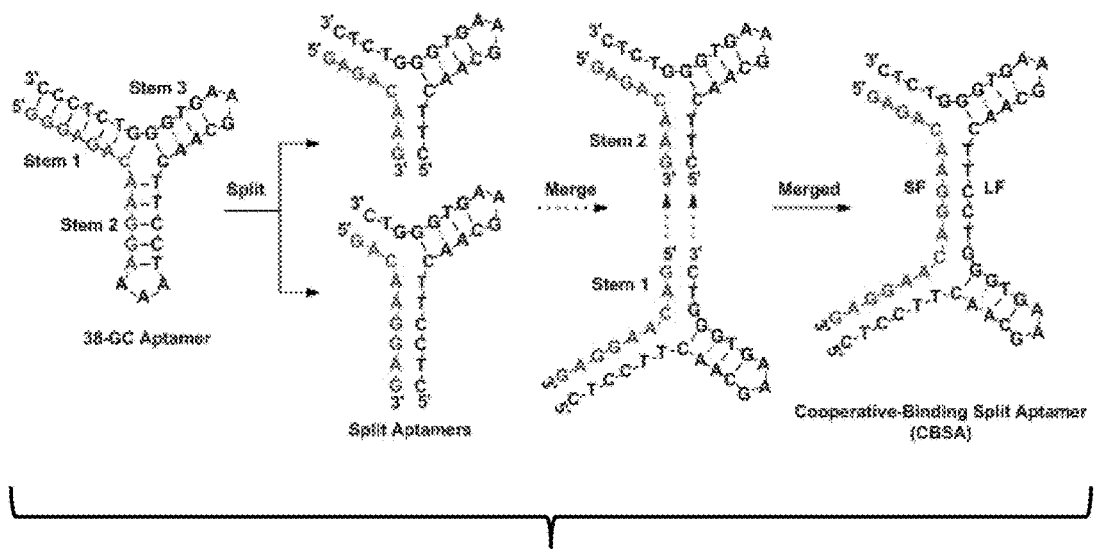
FIG. 16 shows the design process for the cocaine-binding cooperative binding split aptamer (CBSA). The sequence of 38-GC (SEQ ID NO:2) (A) was truncated to form two split aptamer pairs (B). Stem 1 of one set of split aptamers was merged with stem 2 of another set of split aptamers (C) to form an engineered CBSA (D) comprising a short fragment (SF) (SEQ ID NO:29) and a long fragment (LF)) (SEQ ID NO:28).

Target-induced cooperative binding of split aptamers requires the incorporation of at least two target-binding domains into a single pair of fragments. The cocaine-binding aptamer 38-GC (FIG. 16A), an enhanced version of MNS-4.1 with 2.5-fold higher cocaine affinity was used to design CBSAs (D. Roncancio, H. Yu, X. Xu, S. Wu, R. Liu, J. Debord, X. Lou, Y. Xiao, *Anal. Chem.* 2014, 86, 11100-6). 38-GC contains a three-way junction with the target-binding domain located at its center, surrounded by three double-stranded stems (stems 1, 2 and 3) and two loops (AAG and AAA loops). It was previously determined that intact stem 3 is essential for cocaine binding, while stem 1 and stem 2 both contribute to the stability of the target-induced three-way junction structure (D. Roncancio, H. Yu, X. Xu, S. Wu, R. Liu, J. Debord, X. Lou, Y. Xiao, *Anal. Chem.* 2014, 86, 11100-6). Therefore, the stem 3 was left intact and the 3'-end of stem 1 and the AAA loop of stem 2 were truncated to form split aptamers with a single cocaine-binding domain (FIG. 16B), Stem 1 from one set of split aptamers was subsequently merged with stem 2 from a second set of split aptamers (FIG. 16C). The resulting CBSA consists of a short fragment (SF) and a long fragment (LF), which forms two tandem cocaine-binding domains when fully assembled by the target (FIG. 16D). In the absence of target, the fragments were anticipated to remain separated. DNA sequences used to generate the CBSAs are shown below:

| Sequence ID: | Sequence |
|---|---|
| L-5325 | 5'CTCCTTCAACGAAGTGGGT TCCTTCAACGAAGTGGGTCT C3' (SEQ ID NO: 6) |
| S-5325 | 5'GAGACAAGG/iSpC3/ACA AGGAG3' (SEQ ID NO: 7) |
| S-5325-Cy5 | 5'/5IAbRQ/GAGACAAGG/ iSpC3/ACAAGGAGT/ 3Cy5Sp/3' (SEQ ID NO: 8) |
| L-5335 | 5'CTCCTTCAACGAAGTGGGT CTCCTTCAACGAAGTGGGTCT C3' (SEQ ID NO: 9) |
| S-5335 | 5'GAGACAAGG/iSpC3/GAC AAGGAG3' (SEQ ID NO: 10) |
| S-5335-Cy5 | 5'/5IAbRQ/GAGACAAGG/ iSpC3/GACAAGGAGT/ 3Cy5Sp/3' (SEQ ID NO: 11) |
| L-5334 | 5'TCCTTCAACGAAGTGGGTC TCCTTCAACGAAGTGGGTCT C3' (SEQ ID NO: 12) |
| S-5334 | 5'GAGACAAGG/iSpC3/GAC AAGGA3' (SEQ ID NO: 13) |
| L-6225 | 5'CTCCTTCAACGAAGTGGGT TCTTCAACGAAGTGGGTCTC C3' (SEQ ID NO: 14) |
| S-6225 | 5'GGAGACAAG/iSpC3/ACA AGGAG3' (SEQ ID NO: 15) |
| L-4425 | 5'CTCCTTCAACG%AAGTGGG TTCCCTTCAACGAAGTGGGTC T3' (SEQ ID NO: 16) |
| S-4425 | 5'AGACAAGGG/iSpC3/ACA AGGAG3' (SEQ ID NO: 17) |
| L-LSA | 5'CTCCTTCAACGAAGTGGGT TCCTTGTCTC3' (SEQ ID NO: 18) |
| L-SSA | 5'CTCCTTCAACGAAGTGGGT TCC3' (SEQ ID NO: 19) |
| S-SSA | 5'GG/iSpC3/ACAAGGAG3' (SEQ ID NO: 20) |
| L-M1 | 5'CTCCTTCAACGAAGTGGGT TCCTTCGACGAAGTGGGTCT C3' (SEQ ID NO: 21) |
| L-M2 | 5'CTCCTTCGACGAAGTGGGT TCCTTCAACGAAGTGGGTCT C3' (SEQ ID NO: 22) |
| 38-GC | 5'GGGAGACAAGGAAAATCCT TCAACGAAGTGGGTCTCCC3' (SEQ ID NO: 2) |
| 38-GC-20A | 5'GGGAGACAAGGAAAATCCT ACAACGAAGTGGGTCTCCC3' (SEQ ID NO: 23) |
| 38-GC-20C | 5'GGGAGACAAGGAAAATCCT CCAACGAAGTGGGTCTCCC3' (SEQ ID NO: 24) |
| 38-GC-21T | 5'GGGAGACAAGGAAAATCCT TTAACGAAGTGGGTCTCCC3' (SEQ ID NO: 25) |
| 38-GC-22T | 5'GGGAGACAAGGAAAATCCT TCTACGAAGTGGGTCTCCC3' (SEQ ID NO: 26) |
| 38-GC-22G | 5'GGGAGACAAGGAAAATCCT TCGACGAAGTGGGTCTCCC3' (SEQ ID NO: 27) | a. /5IAbRQ/ represents Iowa Black RQ
b. /iSpC3/ represents internal C3 spacer
c. /3Cy5Sp/ represents Cy5
d. S-5325 served as SF for CBSA-5325, LSA, CBSA-M1 and CBSA-M2

Example 12—Characterization of Cocaine-Induced CBSA Assembly

Figure 17A:
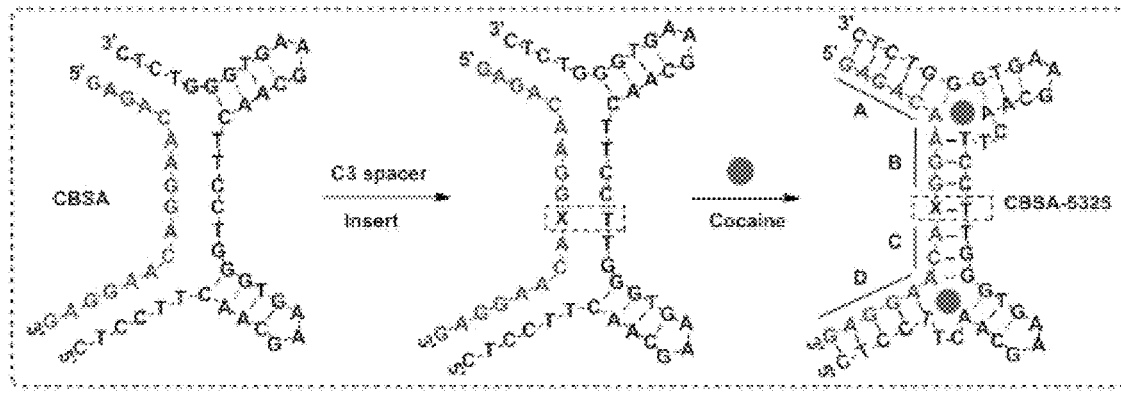
FIGS. 17A-17C show the use of ATMND to report target-induced CBSA assembly. (A) CBSA-5325 (SEQ ID NO:6) incorporates a duplexed AP site capable of binding ATMND. (B) ATMND remains free in solution and generates a fluorescent signal when LF and SF are separate in the absence of cocaine. Upon addition of cocaine, CBSA assembles via cooperative target binding and forms a duplexed AP site that binds and thereby quenches the fluorescence of ATMND. (C) Time-course of ATMND quenching by specific target-induced CBSA assembly.
Figure 17B:
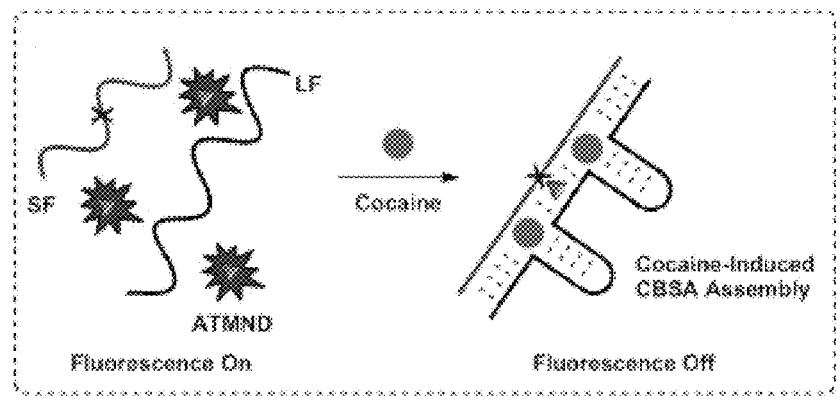

An ATMND-based readout was employed to characterize target-induced CBSA assembly. To achieve this, a C3 spacer was inserted as an apurinic (AP) site between the two binding domains of SF and a thymine (T) at the opposite position in LF. The resulting CBSA-5325 construct contains four segments of complementary base-paired regions (labeled as A-D in FIG. 17A) within the target/aptamer complex. ATMND is well-known for using three-point hydrogen bonding to strongly bind to T nucleotide-containing AP sites ($K_D$=111 nM) (Y. Sato, T. Kageyama, S. Nishizawa, N. Teramae, Anal. Sci. 2013, 29, 15-9). Although ATMND fluoresces brightly when free in solution, this fluorescence is quenched when ATMND is bound to a duplexed AP site located in double-stranded DNA (Y. Sato, S. Nishizawa, K. Yoshimoto, T. Seino, T. Ichihashi, K. Morita, N. Teramae, Nucleic Acids Res. 2009, 37, 1411-22). In the absence of cocaine, LF and SF are expected to remain separated in buffer and the free ATMND molecule generates strong fluorescence (FIG. 17B, left). Upon addition of cocaine, target-binding should induce the assembly of these two CBSA fragments, forming a duplexed AP site that binds ATMND and quenches its fluorescence (FIG. 17B, right). This was confirmed experimentally.

For each ATMND-based fluorescence assay, 10 µL of 10× binding buffer (100 mM Tris, 0.1 mM MgCl2), 85 µL of deionized water, 1 µL of each aptamer fragment (final concentration 1 µM), 1 µL ATMND solution (final concentration 200 nM) and 2 µL of cocaine at different concentrations were mixed into one well of a 96-well plate. Fluorescence intensity was measured using Tecan M1000Pro with excitation at 358 nm and emission at 405 nm at a 2-minute time interval at room temperature until the fluorescence intensity was stable. Each sample was analyzed in triplicate, and the mean and standard deviation of measurements were used in the plots.

Figure 17C:
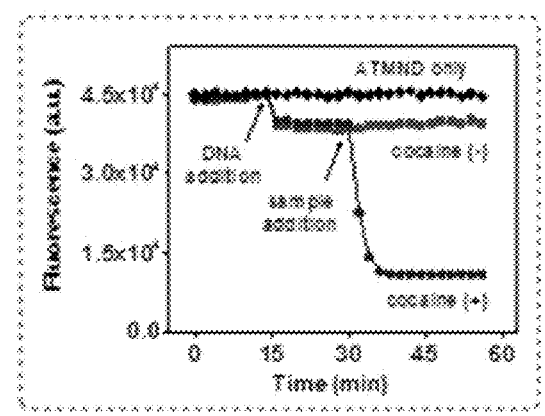
Figure 21:
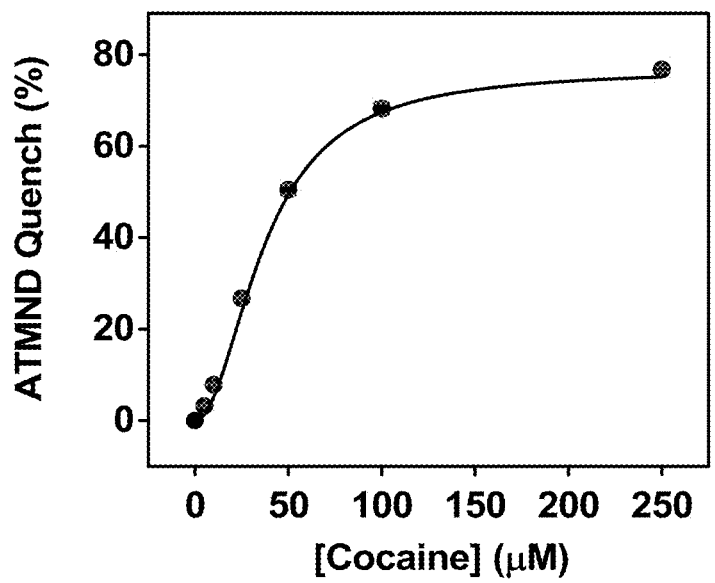
FIG. 21 shows the ATMND-reported calibration curve for cocaine. Error bars show standard deviations from three measurements.
Figure 22:
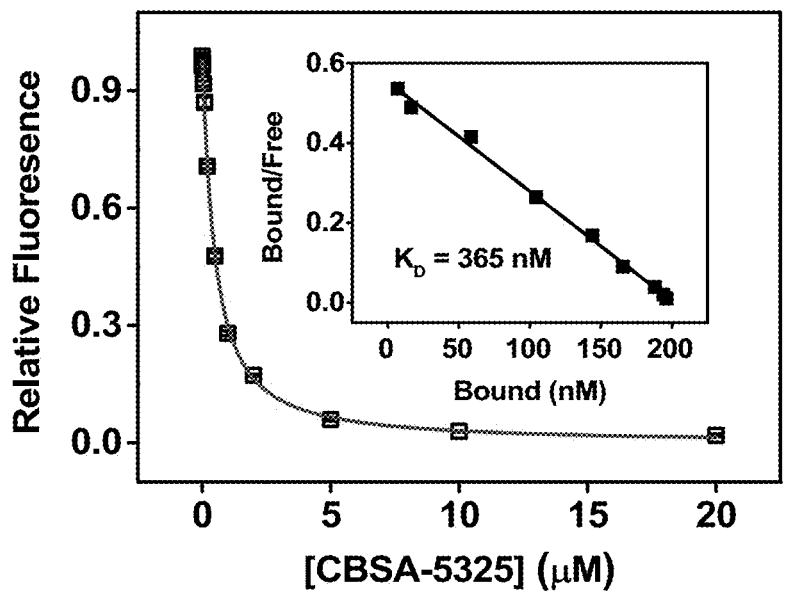
FIG. 22 shows the characterization of ATMND binding affinity for assembled CBSA. The fluorescence of ATMND decreased at increasing concentrations of CBSA-5325 in the presence of 1 mM cocaine concentration upon binding the duplexed AP site within the CBSA structure. Inset: Scatchard plot of the fluorescence data. The KD was determined based on the negative reciprocal of the slope.

When 1 µM each of SF and LF was mixed with 200 nM ATMND in binding buffer (10 mM Tris-HCl+100 µM MgCl2), ~12% background quenching was observed (FIG. 17C, cocaine (−)), possibly due to non-specific interaction between ATMND and the CBSA fragments. Upon addition of 250 µM cocaine, 76% of the ATMND fluorescence was quenched within 10 min, indicating rapid target-induced CBSA assembly (FIG. 17C, cocaine (+)). Aptamer binding affinity (M. N. Stojanovic, P. de Prada, D. W. Landry, *J. Am. Chem. Soc.* 2001, 123, 4928-31; O. Reinstein, M. Yoo, C. Han, T. Palmo, S. a Beckham, M. C. J. Wilce, P. E. Johnson, *Biochemistry* 2013, 52, 8652-62) and DNA hybridization efficiency (R. Owczarzy, B. G. Moreira, Y. You, M. A. Behlke, J. A. Walder, Biochemistry 2008, 47, 5336-53) are both strongly affected by magnesium concentration. To optimize cocaine-induced CBSA assembly, we varied the $Mg^{2+}$ concentration from 10 to 1000 μM, and observed that maximum cocaine-induced ATMND quenching occurred in the presence of 100 μM of $Mg^{2+}$ (FIG. 20A). The ATMND concentration was also varied from 50 to 1000 nM, and determined that the optimal concentration was 200 nM (FIG. 20B). Under these optimized conditions, we generated a calibration curve with cocaine concentrations from 0 to 250 μM that demonstrated a good correlation with ATMND quenching, indicating specific cocaine-induced CBSA assembly (FIG. 21). The binding affinity of ATMND to the target-assembled CBSA in the presence of 1 mM cocaine was characterized by titrating different concentrations (0-20 μM) of CBSA into 200 nM ATMND. The calculated KD was 365 nM (FIG. 22), which is consistent with the value reported in the literature (Y. Sato, T. Kageyama, S. Nishizawa, N. Teramae, *Anal. Sci.* 2013, 29, 15-9.).

Example 13—Confirmation of Cooperative Target Binding

Figure 23A:
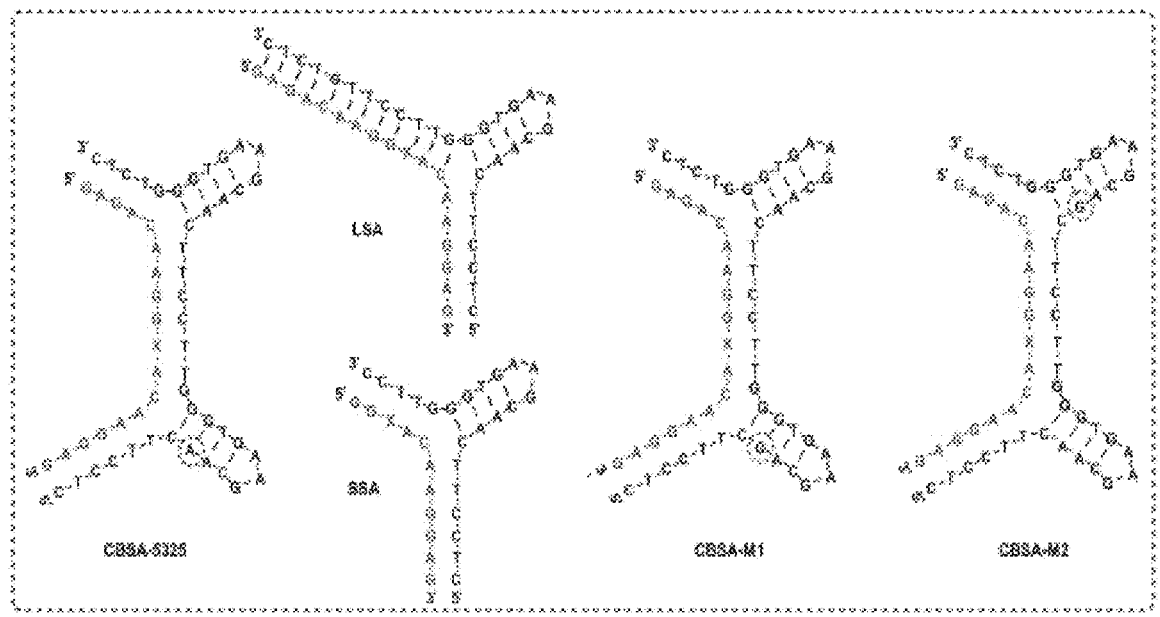
FIGS. 23A-23B show the cooperative binding behavior of CBSA. (A) Sequence of CBSA-5325 (SEQ ID NO:6), split aptamers with single binding pocket (LSA (SEQ ID NO:18) and SSA (SEQ ID NO:19)), and mutants of CBSA-5325 that disrupt either of the two binding pockets (CBSA-M1 (SEQ ID NO:21) and CBSA-M2) (SEQ ID NO:22). (B) ATMND quenching for each of these split aptamer variants with and without 250 μM cocaine. Quenching was calculated by (FA−F)/FA×100%, where FA is the fluorescence of 200 nM ATMND in binding buffer and F is the fluorescence of the ATMND-CBSA mixture with or without 250 μM cocaine. Error bars show standard deviations obtained from three measurements.
Figure 23B:
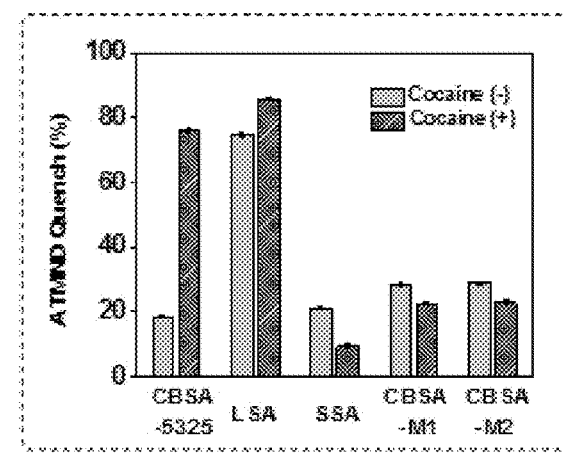

Compared to split aptamers containing a single binding domain, the CBSA fragments are expected to be far more responsive to the presence of cocaine due to the cooperative interaction between their two binding domains. To verify this, one of the binding domains was truncated to generate a short split aptamer (SSA) with only a single cocaine-binding domain (FIG. 23A, SSA). In the absence of cocaine, the SSA achieved 15% quenching of ATMND fluorescence (FIG. 23B), possibly due to non-specific interaction between ATMND and the SSA fragments. No measurable signal change was observed upon addition of 250 μM cocaine. A long split aptamer (LSA) was also produced by replacing one of the binding domains with fully complementary sequences (FIG. 23A, LSA). The LSA fragments quenched 75% of ATMND fluorescence in the absence of cocaine (FIG. 23B), indicating considerable self-assembly of this construct. The addition of 250 μM cocaine yielded only an additional 10% signal change, confirming that the majority of fragments had pre-assembled even in the absence of target (FIG. 23B). In contrast, the CBSA generated a large (76%) signal change upon addition of cocaine by employing the cooperative target binding between its two binding domains.

Figure 24:
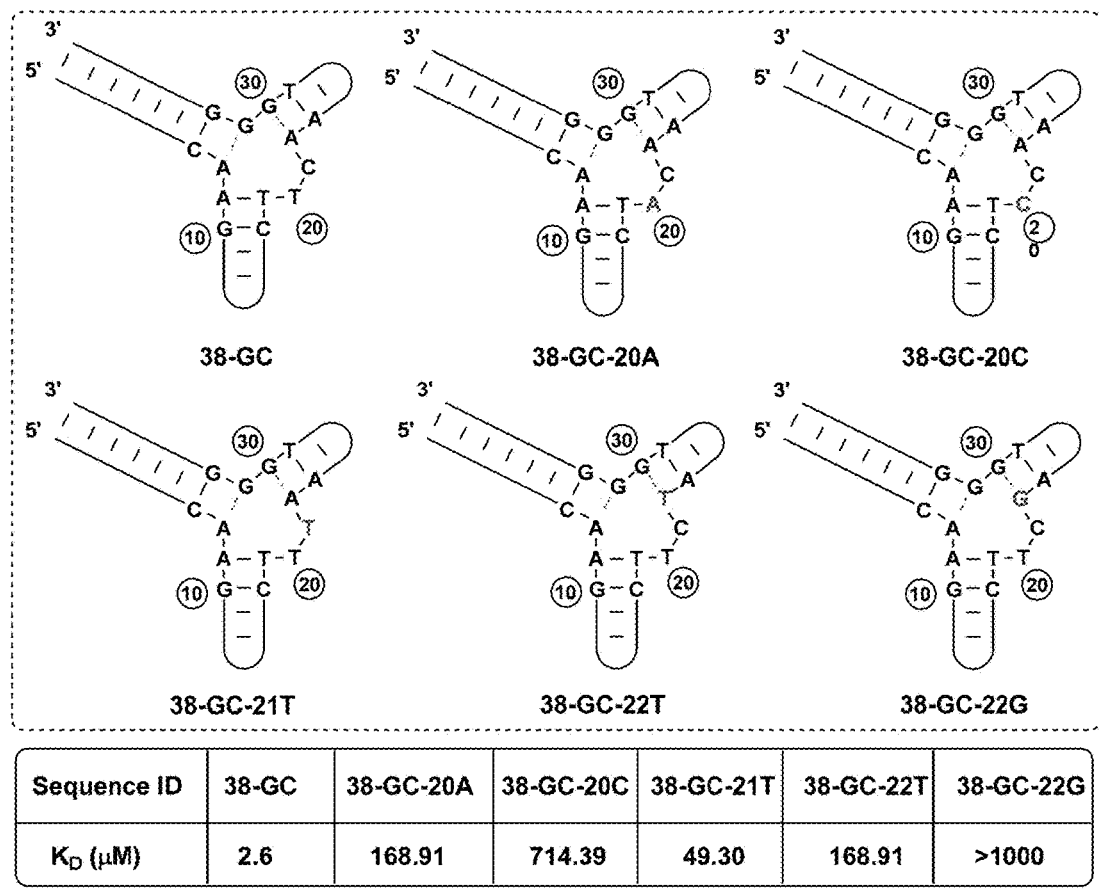
FIG. 24 shows the effects of different mutations to the binding pockets of 38-GC (SEQ ID NO:2) on split aptamer KD, as characterized by ITC.

Both target-binding domains have to work together to achieve cooperative target binding. In order to confirm this, two control CBSAs were designed in which either of the two binding domains was disrupted by a single-nucleotide mutation (FIG. 23A). ITC was used to test a variety of different mutated derivatives of 38-GC (FIG. 24). It was determined that replacing an adenosine at position 22 with a guanine completely impaired cocaine binding (38-GC-22G; FIG. 24). This mutation was used to create CBSA-M1 (with the mutation in LF at the 3'-binding domain) and CBSA-M2 (with the mutation in LF at the 5'-binding domain) (SI, Figure S4A, CBSA-M1 and CBSA-M2). These mutants were tested using the same ATMND-based fluorescence assay, and it was found that neither M1 nor M2 was capable of specific cocaine-induced aptamer assembly, with no significant ATMND quenching observed upon addition of cocaine (FIG. 23B). These results confirmed that both target-binding domains of the CBSA were required to achieve aptamer assembly.

The binding mechanism and affinity of CBSA-5325 for its target was further characterized using ITC. ITC experiments were performed with a MicroCal iTC200 (GE Healthcare). Cocaine and split aptamers were prepared with the binding buffer. The sample cell was initially loaded with 20 μM of single-stranded 38-GC mutants or split aptamers. 4 mM (CBSA-5325, LSA, SSA, CBSA-M1, CBSA-M2) or 2 mM (CBSA-5335) of cocaine titrant was loaded into the syringe. Each experiment typically consisted of 39 successive 1 μL injections after a 0.4 μL purge injection with spacing of 210 seconds to a final molar ratio of 43:1 or 21:1 (cocaine: aptamer). Split-aptamer experiments were performed at 20° C., while experiments with 38-GC mutants were performed at 25° C. The raw data were first corrected based on the heat of dilution of cocaine, and then analyzed with the MicroCal analysis kit integrated into Origin 7 software. The titration curves of the 38-GC mutants, SSA, LSA, CBSA-M1 and CBSA-M2 were fitted with a single-site binding module and the titration curves of CBSA-5325 and CBSA-5335 were fitted with a sequential binding module with two binding sites.

Figure 25A:
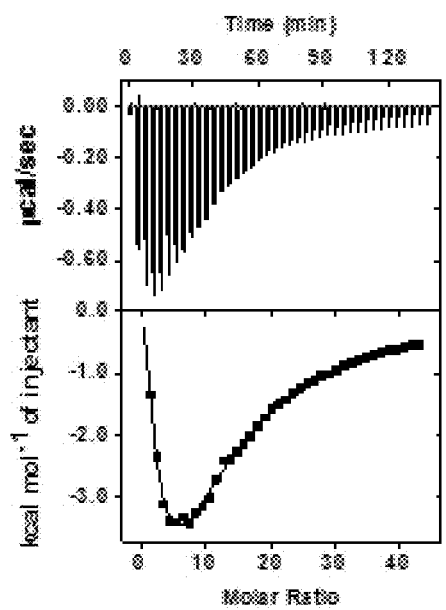
FIGS. 25A-25F show the characterization of cocaine binding affinity of CBSA-5325 (A), LSA (B), SSA (C), CBSA-M1 (D), CBSA-M2 (E) and CBSA-5335 (F) using ITC. Top panels present raw data showing the heat generated from each titration of cocaine. Bottom panels show the integrated heat of each titration after correcting for dilution heat of the titrant.
Figure 25B:
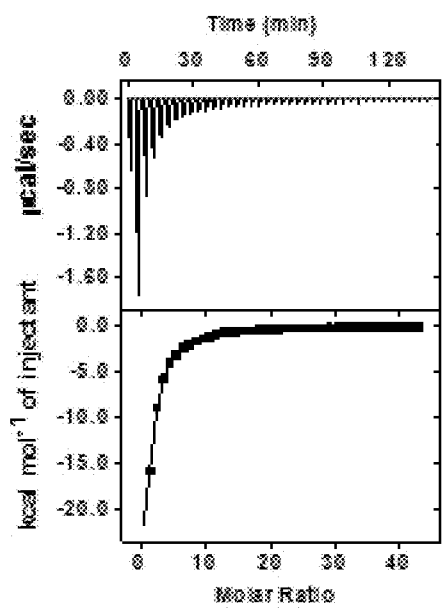
Figure 25C:
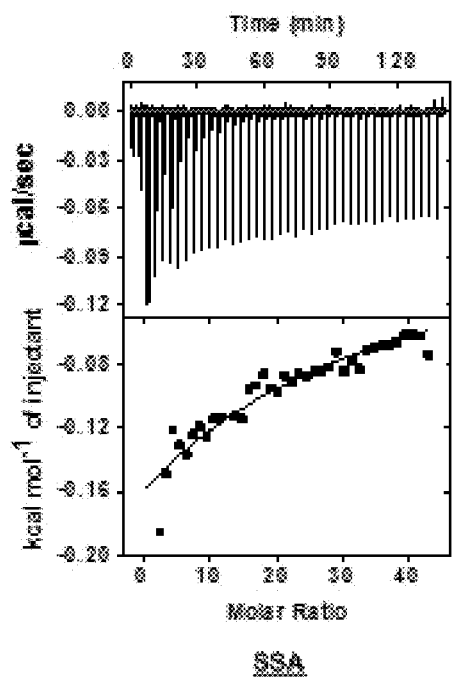
Figure 25D:
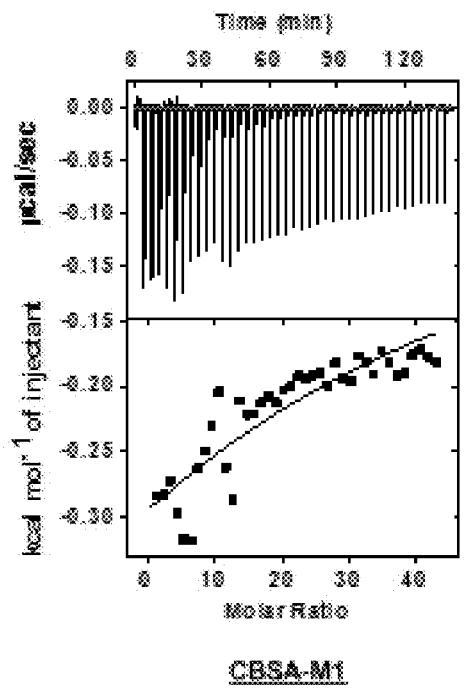
Figure 25E:
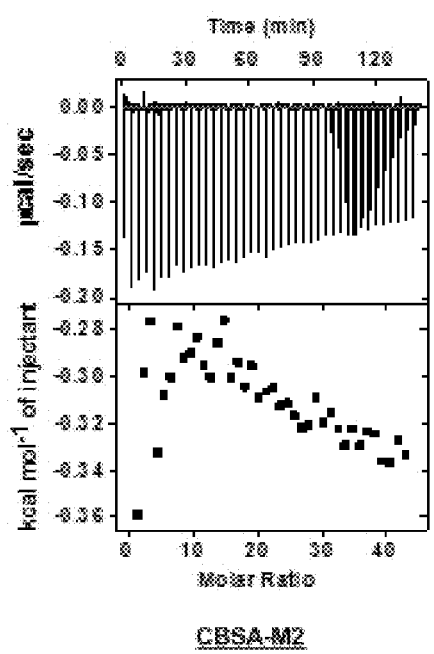

The two-phase titration curve confirmed the interaction of cocaine with the two binding domains of the CBSA (FIGS. 25A and 25F), fitting well with a sequential binding model (M. W. Freyer, E. A. Lewis, Methods Cell Biol. 2008, 84, 79-113). Dissociation constants ($K_D$) of 283 μM and 106 μM were obtained for the first and second cocaine-binding sites, respectively. The 2.7-fold difference between these two $K_D$ values indicates cooperative binding behavior (FIG. 25A). The binding affinities of LSA, SSA, CBSA-M1 and CBSA-M2 (FIG. 25B-E) were also tested. In keeping with the ATMND-based fluorescence data, no specific cocaine binding to SSA, CBSA-M1 or CBSA-M2 was detected, confirming that both binding domains are essential for target-induced CBSA assembly. In contrast, LSA demonstrated strong binding to cocaine in ITC, with a $K_D$ of 32.8 μM. This value is lower than previously reported cocaine-binding split aptamers (M. N. Stojanovic, D. W. Landry, P. de Prada, J. Am. Chem. Soc. 2000, 122, 11547-11548; R. Zou, X. Lou, H. Ou, Y. Zhang, W. Wang, M. Yuan, M. Guan, Z. Luo, Y. Liu, RSC Adv. 2012, 2, 4636-4638) because the 11 complementary base-pairs formed in stem 1 stabilized the three-way-junction.

Example 14—Rational Sequence-Engineering of CBSA

Figure 25F:
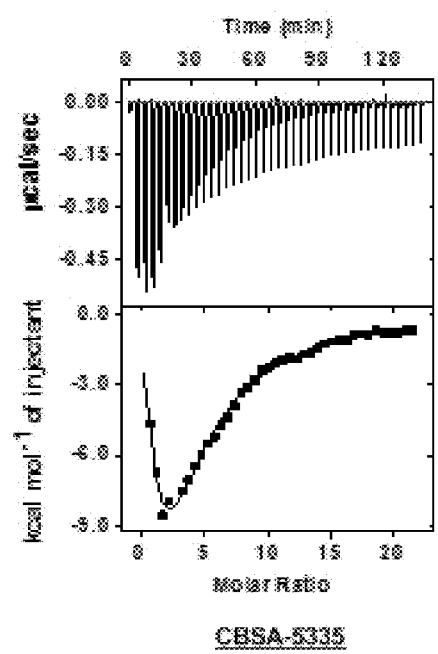
Figure 26A:
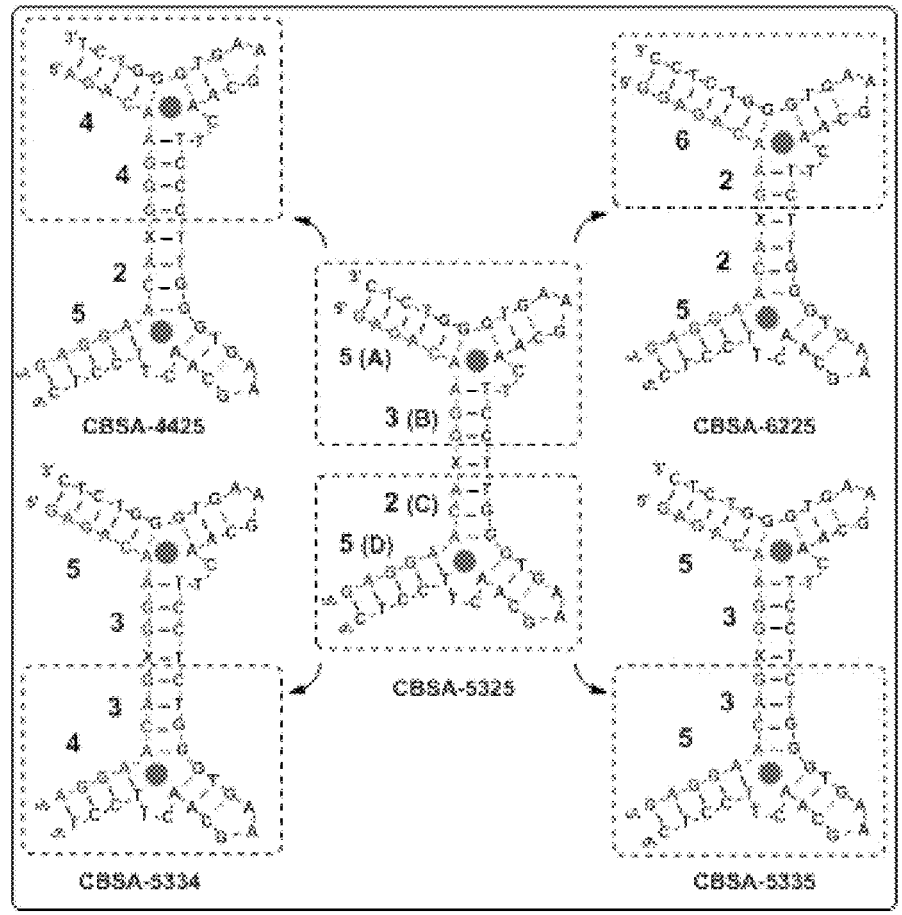
FIGS. 26A-26B show the sequence engineering of CBSA. (A) CBSA-4425 (SEQ ID NO:16) and CBSA-6225 (SEQ ID NO:14) were generated from CBSA-5325 by altering the length of sections A and B, and CBSA-5334 and CBSA-5335 were generated by altering the length of sections C and D. (B) ATMND-reported calibration curve for different CBSAs with cocaine concentrations ranged from 0.1 to 500 µM (top) or 0 to 10 µM (bottom). ATMND quenching was calculated by (F0−F)/F0×100%, where F0 is the fluorescence of the ATMND-CBSA mixture without cocaine and F is the fluorescence of mixtures with different concentrations of cocaine. Error bars show standard deviations from three measurements.
Figure 26B:
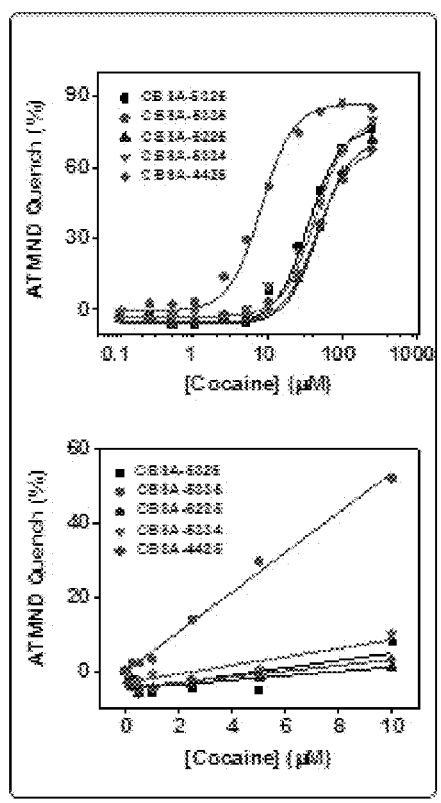

To further improve the sensitivity of the CBSA-based sensor, a series of CBSA-5325 variants were engineered (FIG. 26A). First, the total number of complementary base-pairs was fixed but the number of base-pairs between the two binding domains was increased by moving a base-pair from either end. CBSA-4425 was generated by moving a C-G base-pair from segment A of CBSA-5325 to segment B, while CBSA-5334 was generated by moving a G-C base-pair from segment D of CBSA-5325 to segment C (FIG. 26A). As a result, CBSA-4425 and CBSA-5334 did not show significant differences in cocaine-induced CBSA assembly compared with CBSA-5325, using the ATMND-based fluorescence assay at target concentrations ranging from 0-500 μM (FIG. 26B). Subsequently, the number of complementary base-pairs between the two binding domains in CBSA-5325 was decreased by moving a base-pair from segment B to A to generate CBSA-6225 (FIG. 26A). This CBSA showed similar cocaine binding behavior to CBSA-5325 (FIG. 26B). These results clearly indicated that the cooperative cocaine binding was similar among various types of CBSA containing an identical total of base-pairs. It was hypothesized that the binding affinity of the CBSA might be enhanced by further stabilizing the aptamer-target complex with additional base-pairs, based on prior findings that longer complementary stems surrounding the three-way-junction increased the base aptamer's target-binding affinity (M. a D. Neves, O. Reinstein, P. E. Johnson, Biochemistry 2010, 49, 8478-87). The total number of base-pairs in CBSA-5325 were increased by adding a G-C base-pair into segment C, and the resulting CBSA-5335 construct showed enhanced cocaine-induced aptamer assembly compared to CBSA-5325 (FIG. 26B). ITC analysis of CBSA-5335 determined that the $K_D$ for the first and second cocaine-binding domain of the aptamer were 97.1 and 17.5 µM, respectively, which was 2.9- and 6.1-fold lower than the values measured for CBSA-5325 (FIG. 25F). Therefore, CBSA-5335 was used to fabricate a signal-on fluorescence sensor for ultrasensitive cocaine detection.

Example 15—Fabrication of an Ultra-Sensitive CBSA-Based Fluorescent Sensor

Figure 27:
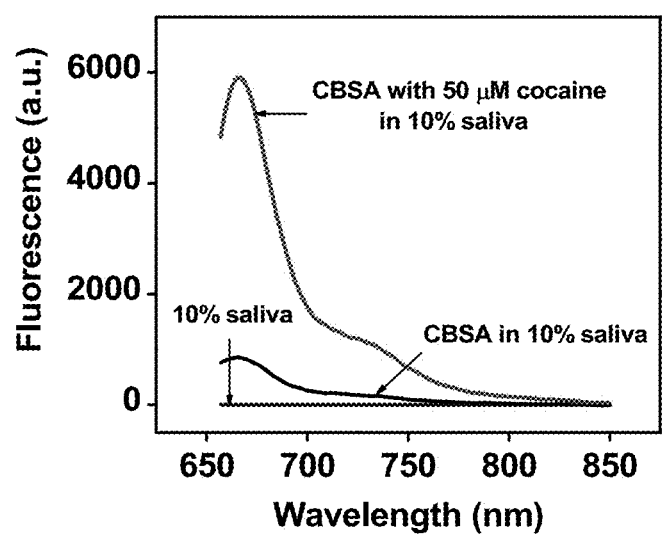
FIG. 27 shows the CBSA-based fluorescent detection of cocaine in saliva. 10% saliva (blue) exhibits no emission from 655 to 850 nm when excited at 648 nm, whereas the addition of the CBSA (black) yields only slight fluorescence background when excited at 648 nm. A significant increase in fluorescence is seen at 668 nm with 50 µM cocaine (red).

A fluorophore/quencher-modified derivative of CBSA-5335 was generated to achieve sensitive detection of cocaine in saliva. Specifically, the SF was modified with an Iowa Black RQ black quencher at its 5' terminus and a Cy5 fluorophore at its 3' terminus. Cy5 was chosen to use because the excitation wavelength for Cy5 (648 nm) is incapable of inducing fluorescence in molecules normally found in saliva matrices (FIG. 27).

Figure 18A:
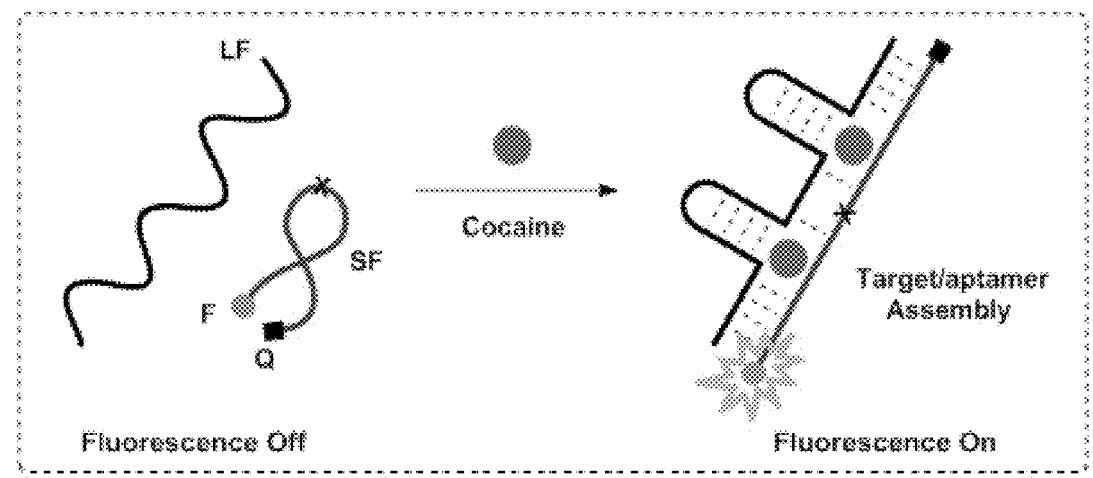
FIGS. 18A-18C show a CBSA-based cocaine fluorescence sensor. (A) The working principle of the CBSA-based fluorescence sensor. A Cy5 fluorophore and an Iowa Black RQ black quencher were respectively attached to the 3' and 5' ends of the SF, such that the fluorophore was quenched by the quencher due to the flexibility of the single-stranded SF in solution. Upon addition of cocaine, CBSA assembly generates a rigid aptamer-target structure that separates the fluorophore from the quencher, resulting in increased fluorescence. (B) The calibration curves for sensors based on CBSA-5325 and CBSA-5335 at cocaine concentrations of 0.05 to 1000 μM. Inset: a linear response was observed for both sensors at 0-25 (C) The response of the CBSA-based sensors at low cocaine concentrations (0-5 μM) demonstrated that CBSA-5335 gave higher target sensitivity, with a greater slope compared to CBSA-5325. Error bars showed the standard deviation of signal gains obtained from three individual measurements at each cocaine concentration.

In the absence of cocaine, the two CBSA fragments remain separate, bringing the fluorophore in close proximity to the quencher due to the flexibility of the single-stranded SF, resulting in very low fluorescence (FIG. 18A, left). When the CBSA is challenged with cocaine, the two fragments assemble to form a rigid aptamer-target structure that separates the fluorophore/quencher pair, generating a fluorescent signal (FIG. 18A, right).

For each CBSA-based fluorophore/quencher assay, 10 µL of 10× binding buffer, 83 µL of deionized water, 1 µL of the CBSA long fragment and 1 µL of the fluorophore/quencher-modified CBSA short fragment (final concentration 1 µM), and 5 µL of cocaine were mixed at different concentrations in one well of a 96-well plate. The fluorescence intensity was measured with a Tecan M1000Pro with excitation at 648 nm and emission at 668 nm at room temperature after 10 min of incubation. Each sample was analyzed in triplicate, and the mean and standard deviation of the measurements was used in the plots. The data was fitted with the Hill equation using Origin 9 software to calculate nH, K1/2, KD1 and KD2. The signal gain was calculated based on (F−F0)/F0, where F is the fluorescence intensity of the cocaine sample and F0 is the fluorescence intensity of the cocaine-free sample.

Figure 18B:
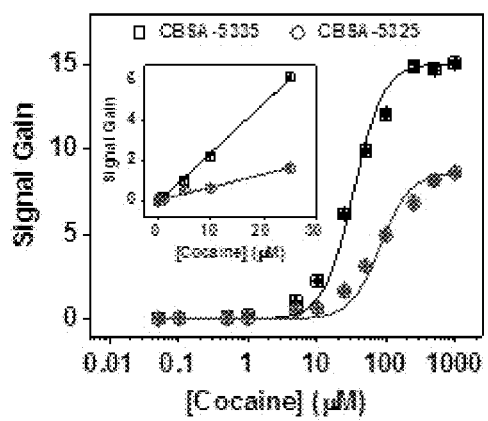
Figure 18C:
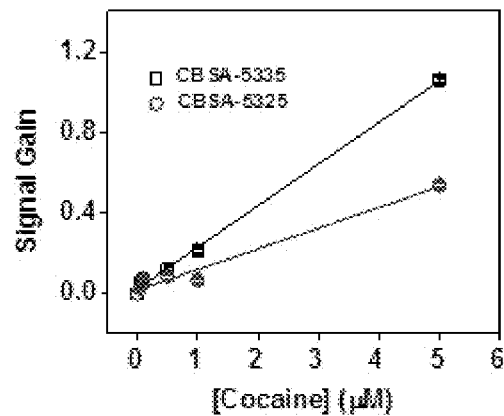

A calibration curve for fluorophore/quencher-modified CBSA-5335 was generated at cocaine concentrations ranging from 0-1000 µM (FIG. 18B). As expected, CBSA-5335 was more sensitive to cocaine concentration compared to CBSA-5325 (FIG. 18C). Since the CBSA uses a cooperative target-binding model, the Hill equation was used to fit the binding curve (A. Hill, J. Physiol. 1910, 40, iv-vii; A. J. Simon, A. Vallée-Bélisle, F. Ricci, K. W. Plaxco, Proc. Natl. Acad. Sci. U.S.A 2014, 111, 15048-53). A $K_{1/2}$ of 33 µM and an $n_H$ of 1.5 was obtained, which is consistent with the results we obtained via ITC ($K_{1/2}$=45 µM, $n_H$=1.3).

$$\text{Binding site occupancy } \overline{Y} = \frac{[\text{Target}]^{n_H}}{[\text{Target}]^{n_H} + (K_{1/2})^{n_H}}$$

Where $K_{1/2}$ represents the target concentration at which half of the binding domains are occupied and the Hill coefficient ($n_H$) describes the order of binding cooperativity. Notably, the low $K_{1/2}$ of the CBSA-5335 demonstrated a higher target binding affinity compared to the cocaine-binding split aptamers reported in other works (M. N. Stojanovic, D. W. Landry, P. de Prada, J. Am. Chem. Soc. 2000, 122, 11547-11548; R. Zou, X. Lou, H. Ou, Y. Zhang, W. Wang, M. Yuan, M. Guan, Z. Luo, Y. Liu, RSC Adv. 2012, 2, 4636-4638). An $n_H$ of 1.5 reveals a high cooperativity between the two binding domains of CBSA-5335. A limit of detection (LOD) of 25 nM was determined based on this calibration curve (FIG. 18C), using the standard of a signal-to-noise ratio ≥3. This LOD is more than 400-fold lower than that of the originally reported split aptamer-based cocaine sensor, which otherwise utilized the same fluorophore-quencher strategy (M. N. Stojanovic, D. W. Landry, P. de Prada, J. Am. Chem. Soc. 2000, 122, 11547-11548).

Example 16—Validation of the CBSA-5335-Based Fluorescence Sensor in Saliva Samples The CBSA-based fluorescence sensor can be used to perform sensitive cocaine detection in saliva samples. Cocaine was first spiked into the pooled saliva to create artificial samples with different concentrations ranging from 0.25 to 500 µM. Each sample was prepared by mixing 10 µL of 10× binding buffer, 1 µL of CBSA-5335 long fragment and 1 µL of fluorophore/quencher modified CBSA-5335 short fragment (final concentration 1 µM) into one well of a 96-well plate. Ten or 50 µL of sample from each cocaine concentration was added into the well to analyze the 10% or 50% saliva matrices and deionized water was added to bring each well's volume to 100 µL. Fluorescence intensity with excitation at 648 nm and emission from 655-850 nm was scanned with a Tecan M1000Pro at room temperature after 10 min of incubation. Each sample was analyzed in triplicate, and the mean and standard deviation of the signal gain at different cocaine concentrations were plotted.

For cocaine detection in 10% saliva, 5 µL of cocaine in solutions of concentrations ranging from 0.001 to 10 µM was mixed with 10 µL of pooled saliva, 10 µl of 10× binding buffer, 1 µL of the CBSA long fragment, 1 µL of the fluorophore/quencher modified CBSA short fragment (final concentration 1 µM), and 73 µL of deionized water in one well of a 96-well plate. Fluorescence intensity with excitation at 648 nm and emission at 668 nm was measured with a Tecan M1000Pro at room temperature after 10 min of incubation. Each sample was analyzed in triplicate, and the mean and standard deviation of the signal gain at different cocaine concentrations were plotted. A control calibration curve in buffer was also performed with cocaine concentrations ranging from 0.001 to 10 µM as described above. LOD was calculated based on the lowest cocaine concentration achieving a signal-to-noise ratio larger than three.

To determine CBSA-5335 sensor specificity, the fluorescence assay was performed as described above with cocaine, cocaethylene, benzoylecgonine, anhydroecgonine methyl ester or nicotine at concentrations of 5 or 50 µM in 10% saliva. Each sample was analyzed in triplicate and the mean and standard deviation of the signal gain at different cocaine concentrations were plotted. The cross-reactivity of each analyte at each concentration was calculated as a percentage based on SigANA/SigCOC×100%, where SigANA is the signal gain achieved by a given interferents and SigCOC is the signal gain achieved by cocaine.

To determine CBSA-5335 sensor precision and bias, the fluorescence assay was performed as described above in 10% diluted saliva matrices collected from eight different donors, 10% diluted pooled saliva matrices and buffer. Six measurements of samples containing final cocaine concentrations of 0, 100, 500 and 1000 nM were performed and the mean and standard deviation of the signal gain were plotted at different cocaine concentrations. The bias of each cocaine concentration was calculated as (Meansam−Meanpool)/Meanpool×100%, where Meansam is the mean signal gain obtained in 10% saliva matrices collected from different donors, and Meanpool is the mean signal gain obtained in the 10% pooled saliva matrices. The precision within samples or between runs at different cocaine concentrations was calculated by performing a one-way ANOVA test with the measurement number (6) as the grouping variable. Within-sample precision at each cocaine level was calculated as $\sqrt{MS_{wg}}/Mean_{sam}\times 100\%$, where MSwg is the within-group mean square obtained from the ANOVA table, and Meansam is the mean of signal gains obtained in 10% saliva matrices collected from different donors. Between-run precision at each cocaine level was calculated as $$\sqrt{\frac{MS_{bg} + (n-1)\times MS_{wg}}{n}} / Mean_{sam} \times 100\%,$$

where MSbg is the between-group mean square obtained from the ANOVA table, and n is the total number of measurements (n=6).

Figure 28:
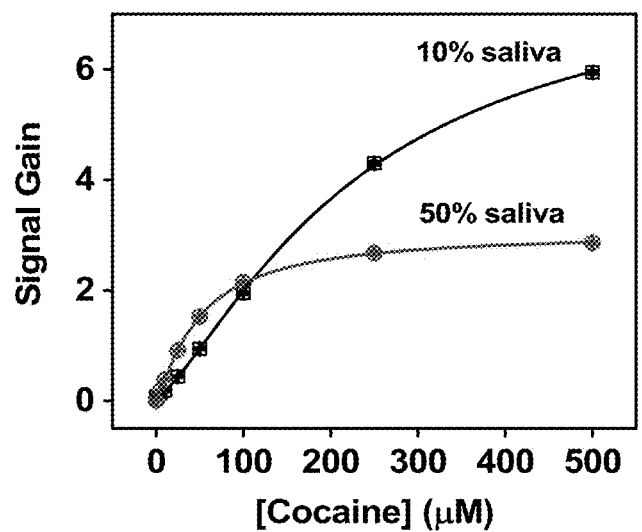
FIG. 28 shows the dilution effects on cocaine detection in saliva. Saliva samples spiked with cocaine were tested with the CBSA-5335-based sensor after 2- or 10-fold dilution. Calibration curves were constructed based on signal gain at each concentration of cocaine in saliva before dilution. The signal gain was calculated by (F−F0)/F0×100%, where F0 is the fluorescence of the CBSA without cocaine and F is the fluorescence of the CBSA with different concentrations of cocaine. Error bars show standard deviations obtained from three measurements.
Figure 29:
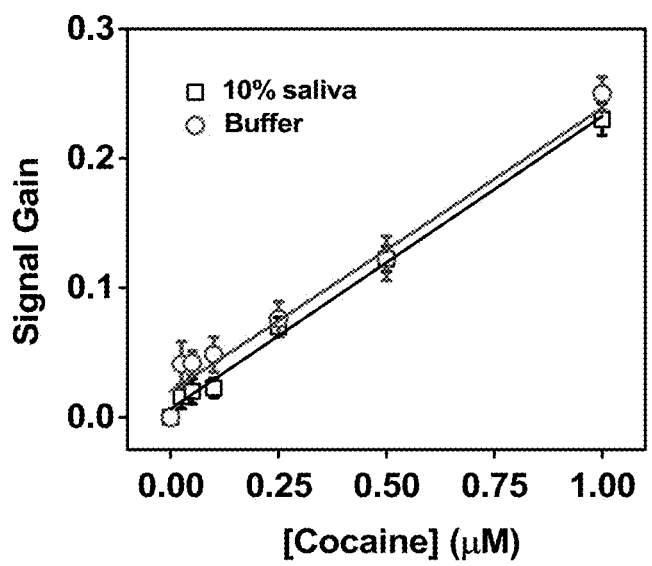
FIG. 29 shows the calibration curve for the CBSA-5335-based cocaine sensor in binding buffer and 10% saliva at different cocaine concentrations ranged from 0 to 1000 nM. Error bars show the standard deviation of signal gains obtained from three measurements at each concentration.

For example, eight different saliva samples collected from healthy, drug-free donors of diverse gender and ethnic backgrounds were mixed as a pooled matrix. This was spiked with different concentrations of cocaine (0 to 500 μM) and diluted with binding buffer to 1:2 (50%) or 1:10 (10%) levels before being applied to the CBSA-5335-based fluorescence sensor. The experimental results showed that matrices with 1:10 dilution gave a broader dynamic range (0-100 μM) compared to 1:2 dilution (0-25 μM) (FIG. 28). Additionally, the higher dilution fold (1:10) reduced the interference from individual saliva matrices, therefore, 10% saliva samples were used for subsequent experiments. To identify the sensor's sensitivity in this matrix, a calibration curve in 10% saliva samples was generated and a linear range from 0 to 10 μM and a LOD of 50 nM was obtained (FIG. 19A; FIG. 29). It has been reported that the cocaine concentration in saliva is usually higher than that in serum within a few hours of administration (H. Gjerde, K. Langel, D. Favretto, A. G. Verstraete, J. Anal. Toxicol. 2014, 38, 92-8; W. Schramm, P. A. Craig, R. H. Smith, G. E. Berger, Clin. Chem. 1993, 39, 481-7), and 170 ng/mL (510 nM) was recommended by the European Union's DRUID (Driving under the Influence of Drugs, Alcohol and Medicines) program as a lower-limit for road-side screening of cocaine in oral fluids (E. J. Cone, M. Hillsgrove, W. D. Darwin, Clin. Chem. 1994, 40, 1299-305). This suggests that, with the incorporation of a preliminary ten-fold sample dilution step, the CBSA-based sensor of the subject invention could be suitable for on-site detection of cocaine (with a LOD equivalent to 500 nM in undiluted saliva).

The CBSA-based sensor of the subject invention also showed excellent target specificity. Benzoylecgonine, anhydroecgonine methyl ester and cocaethylene are major structurally-similar metabolites of cocaine that are secreted into oral fluids (E. J. Cone, M. Hillsgrove, W. D. Darwin, Clin. Chem. 1994, 40, 1299-305) and are known to cross-react with cocaine-binding antibodies (G. Cooper, L. Wilson, C. Reid, D. Baldwin, C. Hand, V. Spiehler, J. Anal. Toxicol. 2004, 28, 498-503; V. Spiehler, J. Fay, R. Fogerson, D. Schoendorfer, R. Niedbala, Clin. Chem. 1996, 42, 34-38). Benzoylecgonine tetrahydrate, (−) nicotine, anhydroecgonine methyl ester and cocaethylene were purchased from Cerilliant Corporation and were prepared to 50 mM stock solution in deionized water and stored at 4° C. The CBSA-based sensor of the subject invention was challenged with high concentrations of these metabolites as well as nicotine, since tobacco is widely used among cocaine users (S. T. Higgins, JAMA J. Am. Med. Assoc. 1994, 272, 1724). The results demonstrated no measurable signal from 500 μM of benzoylecgonine, anhydroecgonine methyl ester or nicotine in undiluted saliva. Nineteen percent and three percent cross-reactivity to 500 μM and 50 μM cocaethylene in undiluted saliva was observed, respectively. Compared to commercial available immunoassays that often have high cross-reactivity to cocaine metabolites (G. Cooper, L. Wilson, C. Reid, D. Baldwin, C. Hand, V. Spiehler, J. Anal. Toxicol. 2004, 28, 498-503; V. Spiehler, J. Fay, R. Fogerson, D. Schoendorfer, R. Niedbala, Clin. Chem. 1996, 42, 34-38), such as the Cozart microplate EIA assay for cocaine (G. Cooper, L. Wilson, C. Reid, D. Baldwin, C. Hand, V. Spiehler, J. Anal. Toxicol. 2004, 28, 498-503) (77% and 220% cross-reactivity to benzoylecgonine and cocaethylene, respectively), the CBSA-based sensor of the subject invention clearly represents higher target specificity in oral fluids (FIG. 19B).

Figures 30A, 30B:
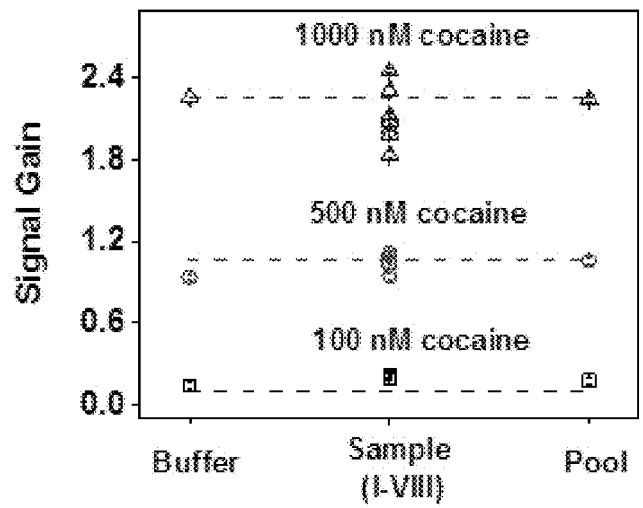
FIGS. 30A-30B show the bias and precision of the CBSA-5335-based cocaine sensor. (A) Signal gain obtained from various cocaine concentrations in different matrices including buffer, 10% saliva collected from different donors (Sample I-VIII) and 10% pooled saliva. Signal gain was calculated by (F−F0)/F0×100%, where F0 is the fluorescence of the CBSA without cocaine and F is the fluorescence of the CBSA with cocaine. Error bars show standard deviations from six measurements. (B) Bias at each cocaine concentration was calculated from the mean value of signal gain obtained with samples I-VIII and the pooled sample. Within-sample and between-run precision at each cocaine concentration was calculated by one-way ANOVA.

The bias and precision of the CBSA-based sensor for real samples was further tested by spiking 10% saliva samples from eight different individuals with 100, 500 or 1000 nM cocaine (FIG. 30A). Using the pooled saliva as a standard, the average bias of signal gain obtained in these individual samples was 12.7%, −0.4% and −5.8% at 100, 500 and 1000 nM cocaine, respectively. At 100, 500 and 1,000 nM, the coefficients of variation (CV) within samples were 7.1%, 5.2% and 9.0%, respectively (FIG. 30B), and the CVs between runs were 7.3%, 5.1% and 8.5%, respectively (FIG. 30B). Thus, the bias and CV at all cocaine levels was below the acceptable cut-off (20%) for drug-screening methods (J. Anal. Toxicol. 2013, 37, 452-74) further demonstrating the feasibility of the CBSA-based sensor of the subject invention for performing rapid and specific on-site screening.

REFERENCES

1. Stojanovic, M. N.; Landry, D. W. *J Am. Chem. Soc.* 2002, 124, 9678-9679.
2. Zheng, D.; Zou, R.; Lou, X. *Anal. Chem.* 2012, 84, 3554-3560.
3. He, J. L.; Wu, Z. S.; Zhou, H.; Wang, H. Q.; Jiang, J. H.; Shen, G.; Yu, R. Q. *Anal. Chem.* 2010, 82, 1358-1364.
4. Stojanovic, M. N.; Prada, P.; Landry, D. W. *J Am. Chem. Soc.* 2000, 122, 11547-11548.
5. Du, Y.; Li, B.; Guo, S.; Zhou, Z.; Zhou, M.; Wang, E.; Dong, S. *Analyst* 2011, 136, 493-497.
6. Stojanovic, M. N.; Prada, P.; Landry, D. W. *J. Am. Chem. Soc.* 2001, 123, 4928-4931.
7. Liu, J.; Lu, Y. *Angew. Chem. Int. Ed* 2006, 45, 90-94.
8. Kang, K.; Sachan, A.; Nilsen-Hamilton, M.; Shrotriya, P. *Langmuir* 2011, 27, 14696-14702.
9. Baker, B. R.; Lai, R. Y.; Wood, M. S.; Doctor, E. H.; Heeger, A. J.; Plaxco, K. W. *J. Am. Chem. Soc.* 2006, 128, 3138-3139.

We claim:

1. An aptamer that binds both cocaine and 2-amino-5,6,7-trimethyl-1,8-naphthyridine (ATMND), wherein said aptamer is derived from MNS-4.1, wherein said derivation comprises the conversion of at least one non-canonical base pair to a Watson-Crick base pair, wherein the aptamer is not modified at either the T21 or the A23 position relative to MNS-4.1, wherein said aptamer has increased stability, and wherein said aptamer binds cocaine more strongly than ATMND.

2. The aptamer, according to claim 1, wherein the equilibrium dissociation constant for binding to cocaine is 5.0 μM or less.

3. The aptamer, according to claim 1, wherein at least 95% of the fluorescence of the ATMND is quenched in the absence of cocaine.

4. The aptamer, according to claim 1, which is 38-GC or 38-GT.

5. A method for detecting cocaine in a biological sample wherein said method comprises contacting said sample with an aptamer according to claim 1 to which 2-amino-5,6,7-trimethyl-1,8-naphthyridine (ATMND) is bound and determining whether an increase in fluorescence occurs, wherein an increase in fluorescence is indicative of the presence of cocaine in the sample.

6. The method, according to claim 5, wherein said aptamer is derived from MNS-4.1, wherein said derivation comprises the addition of complementary base pairs at multiple sites that confer upon the aptamer increased stability, wherein the aptamer is not modified at either the C21 or the T20 position relative to MNS-4.1.

7. The method, according to claim 5, wherein the aptamer is 38-GC or 38-GT.

8. The method, according to claim 5, wherein a molar ratio of the aptamer to ATMND of 8:1 is utilized.

9. The method, according to claim 5, wherein the biological sample is selected from the group consisting of saliva, urine, and serum.

10. The method, according to claim 5, wherein at least 95% of the fluorescence of the ATMND is quenched when cocaine is not present.

11. The method, according to claim 5, wherein a signal gain of at least 10 is obtained in the presence of 50 μM of cocaine.

12. A cooperative-binding split aptamer (CBSA) derived from two molecules of MNS-4.1, the CBSA having a short and a long fragment, wherein the aptamer comprises two cocaine binding domains and an ATMND-binding site when the short and long fragment associate in the presence of cocaine; wherein cocaine binding to a first cocaine binding domain greatly increases the affinity of the second cocaine binding domain; wherein the CBSA comprises at least one non-canonical base pair converted to a Watson-Crick base pair; wherein the CBSA is not modified at either of the positions corresponding to T21 and A23 of MNS-4.1; and wherein the CBSA further comprises at least one additional Watson-Crick base pair added between the two cocaine-binding domains.

13. The aptamer, according to claim 12, wherein the addition of one Watson-Crick base pair confers enhanced cocaine-induced aptamer assembly.

14. The cooperative-binding split aptamer according to claim 12, wherein said short fragment comprises a quencher at the 5' terminus and a fluorophore at the 3' terminus, which said quencher is in close proximity to said fluorophore in the absence of cocaine; wherein cocaine binding to a first cocaine binding domain increases the affinity of the second cocaine binding domain; wherein the short and long fragment associate in the presence of cocaine thereby creating a rigid aptamer-cocaine structure that separates said quencher and said fluorophore; and wherein an increase in fluorescence is indicative of the presence of cocaine.

15. The cooperative-binding split aptamer, according to claim 14, wherein the quencher is an Iowa Black RQ black quencher and the fluorophore is Cy 5.

16. A method for detecting cocaine in a biological sample wherein said method comprises contacting said sample with a split aptamer of claim 12, and wherein a decrease in fluorescence of ATMND is indicative of the presence of cocaine.

17. The method, according to claim 16, wherein at least 76% of the fluorescence of ATMND fluorescence is quenched, after the sample is contacted with the aptamer.

18. The method, according to claim 16, wherein a signal gain of at least 6 is obtained in the presence of 25 μM cocaine.

* * * * *

SEQUENCE LISTING

<160> NUMBER OF SEQ ID NOS: 29

<210> SEQ ID NO 1
<211> LENGTH: 38
<212> TYPE: DNA
<213> ORGANISM: Artificial
<220> FEATURE:
<223> OTHER INFORMATION: nucleic acid sequence of aptamer 38-GT

<400> SEQUENCE: 1
gggagacaag gaaaatcctt caatgaagtg ggtctccc        38

<210> SEQ ID NO 2
<211> LENGTH: 38
<212> TYPE: DNA
<213> ORGANISM: Artificial
<220> FEATURE:
<223> OTHER INFORMATION: nucleic acid sequence of aptamer 38-GC

<400> SEQUENCE: 2
gggagacaag gaaaatcctt caacgaagtg ggtctccc        38

<210> SEQ ID NO 3
<211> LENGTH: 38
<212> TYPE: DNA
<213> ORGANISM: Artificial
<220> FEATURE:
<223> OTHER INFORMATION: nucleic acid sequence of aptamer 38-GC M1

<400> SEQUENCE: 3
gggagacaag gaaaatcctc taacgaagtg ggtctccc        38

<210> SEQ ID NO 4
<211> LENGTH: 38
<212> TYPE: DNA
<213> ORGANISM: Artificial
<220> FEATURE:
<223> OTHER INFORMATION: nucleic acid sequence of aptamer 38-GC M2

<400> SEQUENCE: 4
gggagacaag gaaaatccta caacgaagtg ggtctccc        38

<210> SEQ ID NO 5
<211> LENGTH: 39
<212> TYPE: DNA
<213> ORGANISM: Artificial
<220> FEATURE:
<223> OTHER INFORMATION: nucleic acid sequence of aptamer MNS-4.1

<400> SEQUENCE: 5
gggagacaag gataaatcct tcaatgaagt gggtcgata        39

<210> SEQ ID NO 6
<211> LENGTH: 40
<212> TYPE: DNA
<213> ORGANISM: Artificial
<220> FEATURE:
<223> OTHER INFORMATION: nucleic acid sequence of the long fragment of
      CBSA-5325

<400> SEQUENCE: 6
ctccttcaac gaagtgggtt ccttcaacga agtgggtctc        40

<210> SEQ ID NO 7
<211> LENGTH: 18
<212> TYPE: DNA

-continued

<213> ORGANISM: Artificial
<220> FEATURE:
<223> OTHER INFORMATION: nucleic acid sequence of the short fragment of
      CBSA-5325
<220> FEATURE:
<221> NAME/KEY: misc_binding
<222> LOCATION: (10)..(10)
<223> OTHER INFORMATION: apurinic site

<400> SEQUENCE: 7
gagacaagga acaaggag                                                18

<210> SEQ ID NO 8
<211> LENGTH: 19
<212> TYPE: DNA
<213> ORGANISM: Artificial
<220> FEATURE:
<223> OTHER INFORMATION: nucleic acid sequence of the short fragment of
      CBSA-5325-Cy5
<220> FEATURE:
<221> NAME/KEY: misc_feature
<222> LOCATION: (1)..(1)
<223> OTHER INFORMATION: Iowa Black RQ-bound guanine
<220> FEATURE:
<221> NAME/KEY: misc_binding
<222> LOCATION: (10)..(10)
<223> OTHER INFORMATION: apurinic site
<220> FEATURE:
<221> NAME/KEY: misc_feature
<222> LOCATION: (19)..(19)
<223> OTHER INFORMATION: Cy5-bound thymine

<400> SEQUENCE: 8
gagacaagga acaaggagt                                               19

<210> SEQ ID NO 9
<211> LENGTH: 41
<212> TYPE: DNA
<213> ORGANISM: Artificial
<220> FEATURE:
<223> OTHER INFORMATION: nucleic acid sequence of the long fragment of
      CBSA-5335

<400> SEQUENCE: 9
ctccttcaac gaagtgggtc tccttcaacg aagtgggtct c                       41

<210> SEQ ID NO 10
<211> LENGTH: 19
<212> TYPE: DNA
<213> ORGANISM: Artificial
<220> FEATURE:
<223> OTHER INFORMATION: nucleic acid sequence of the short fragment of
      CBSA-5335
<220> FEATURE:
<221> NAME/KEY: misc_binding
<222> LOCATION: (10)..(10)
<223> OTHER INFORMATION: apurinic site

<400> SEQUENCE: 10
gagacaagga gacaaggag                                               19

<210> SEQ ID NO 11
<211> LENGTH: 20
<212> TYPE: DNA
<213> ORGANISM: Artificial
<220> FEATURE:
<223> OTHER INFORMATION: nucleic acid sequence of the short fragment of
      CBSA-5335-Cy5
<220> FEATURE:
<221> NAME/KEY: misc_feature
<222> LOCATION: (1)..(1)

```
<223> OTHER INFORMATION: Iowa Black RQ-bound guanine
<220> FEATURE:
<221> NAME/KEY: misc_binding
<222> LOCATION: (10)..(10)
<223> OTHER INFORMATION: apurinic site
<220> FEATURE:
<221> NAME/KEY: misc_feature
<222> LOCATION: (20)..(20)
<223> OTHER INFORMATION: Cy5-bound thymine

<400> SEQUENCE: 11
gagacaagga gacaaggagt                                                  20

<210> SEQ ID NO 12
<211> LENGTH: 40
<212> TYPE: DNA
<213> ORGANISM: Artificial
<220> FEATURE:
<223> OTHER INFORMATION: nucleic acid sequence of the long fragment of
      CBSA-5334

<400> SEQUENCE: 12
tccttcaacg aagtgggtct ccttcaacga agtgggtctc                             40

<210> SEQ ID NO 13
<211> LENGTH: 18
<212> TYPE: DNA
<213> ORGANISM: Artificial
<220> FEATURE:
<223> OTHER INFORMATION: nucleic acid sequence of the short fragment of
      CBSA-5334
<220> FEATURE:
<221> NAME/KEY: misc_binding
<222> LOCATION: (10)..(10)
<223> OTHER INFORMATION: apurinic site

<400> SEQUENCE: 13
gagacaagga gacaagga                                                    18

<210> SEQ ID NO 14
<211> LENGTH: 40
<212> TYPE: DNA
<213> ORGANISM: Artificial
<220> FEATURE:
<223> OTHER INFORMATION: nucleic acid sequence of the long fragment of
      CBSA-6225

<400> SEQUENCE: 14
ctccttcaac gaagtgggtt cttcaacgaa gtgggtctcc                             40

<210> SEQ ID NO 15
<211> LENGTH: 18
<212> TYPE: DNA
<213> ORGANISM: Artificial
<220> FEATURE:
<223> OTHER INFORMATION: nucleic acid sequence of the short fragment of
      CBSA-6225
<220> FEATURE:
<221> NAME/KEY: misc_binding
<222> LOCATION: (10)..(10)
<223> OTHER INFORMATION: apurinic site

<400> SEQUENCE: 15
ggagacaaga acaaggag                                                    18

<210> SEQ ID NO 16
<211> LENGTH: 40
<212> TYPE: DNA
<213> ORGANISM: Artificial
```

```
<220> FEATURE:
<223> OTHER INFORMATION: nucleic acid sequence of the long fragment of
      CBSA-4425

<400> SEQUENCE: 16
ctccttcaac gaagtgggtt cccttcaacg aagtgggtct                              40

<210> SEQ ID NO 17
<211> LENGTH: 18
<212> TYPE: DNA
<213> ORGANISM: Artificial
<220> FEATURE:
<223> OTHER INFORMATION: nucleic acid sequence of the short fragment of
      CBSA-4425
<220> FEATURE:
<221> NAME/KEY: misc_binding
<222> LOCATION: (10)..(10)
<223> OTHER INFORMATION: apurinic site

<400> SEQUENCE: 17
agacaaggga acaaggag                                                      18

<210> SEQ ID NO 18
<211> LENGTH: 29
<212> TYPE: DNA
<213> ORGANISM: Artificial
<220> FEATURE:
<223> OTHER INFORMATION: nucleic acid sequence of the long fragment of
      CBSA-LSA

<400> SEQUENCE: 18
ctccttcaac gaagtgggtt ccttgtctc                                          29

<210> SEQ ID NO 19
<211> LENGTH: 22
<212> TYPE: DNA
<213> ORGANISM: Artificial
<220> FEATURE:
<223> OTHER INFORMATION: nucleic acid sequence of the long fragment of
      CBSA-SSA

<400> SEQUENCE: 19
ctccttcaac gaagtgggtt cc                                                 22

<210> SEQ ID NO 20
<211> LENGTH: 11
<212> TYPE: DNA
<213> ORGANISM: Artificial
<220> FEATURE:
<223> OTHER INFORMATION: nucleic acid sequence of the short fragment of
      CBSA-SSA
<220> FEATURE:
<221> NAME/KEY: misc_binding
<222> LOCATION: (3)..(3)
<223> OTHER INFORMATION: apurinic site

<400> SEQUENCE: 20
ggaacaagga g                                                             11

<210> SEQ ID NO 21
<211> LENGTH: 40
<212> TYPE: DNA
<213> ORGANISM: Artificial
<220> FEATURE:
<223> OTHER INFORMATION: nucleic acid sequence of the long fragment of
      CBSA-M1

<400> SEQUENCE: 21
```
ctccttcaac gaagtgggtt ccttcgacga agtgggtctc                                40

<210> SEQ ID NO 22
<211> LENGTH: 40
<212> TYPE: DNA
<213> ORGANISM: Artificial
<220> FEATURE:
<223> OTHER INFORMATION: nucleic acid sequence of the long fragment of
      CBSA-M2

<400> SEQUENCE: 22
ctccttcgac gaagtgggtt ccttcaacga agtgggtctc                                40

<210> SEQ ID NO 23
<211> LENGTH: 38
<212> TYPE: DNA
<213> ORGANISM: Artificial
<220> FEATURE:
<223> OTHER INFORMATION: nucleic acid sequence of aptamer 38-GC-20A

<400> SEQUENCE: 23
gggagacaag gaaaatccta caacgaagtg ggtctccc                                  38

<210> SEQ ID NO 24
<211> LENGTH: 38
<212> TYPE: DNA
<213> ORGANISM: Artificial
<220> FEATURE:
<223> OTHER INFORMATION: nucleic acid sequence of aptamer 38-GC-20C

<400> SEQUENCE: 24
gggagacaag gaaaatcctc caacgaagtg ggtctccc                                  38

<210> SEQ ID NO 25
<211> LENGTH: 38
<212> TYPE: DNA
<213> ORGANISM: Artificial
<220> FEATURE:
<223> OTHER INFORMATION: nucleic acid sequence of aptamer 38-GC-21T

<400> SEQUENCE: 25
gggagacaag gaaaatcctt taacgaagtg ggtctccc                                  38

<210> SEQ ID NO 26
<211> LENGTH: 38
<212> TYPE: DNA
<213> ORGANISM: Artificial
<220> FEATURE:
<223> OTHER INFORMATION: nucleic acid sequence of aptamer 38-GC-22T

<400> SEQUENCE: 26
gggagacaag gaaaatcctt ctacgaagtg ggtctccc                                  38

<210> SEQ ID NO 27
<211> LENGTH: 38
<212> TYPE: DNA
<213> ORGANISM: Artificial
<220> FEATURE:
<223> OTHER INFORMATION: nucleic acid sequence of aptamer 38-GC-22G

<400> SEQUENCE: 27
gggagacaag gaaaatcctt cgacgaagtg ggtctccc                                  38

<210> SEQ ID NO 28
<211> LENGTH: 39
<212> TYPE: DNA

```
<213> ORGANISM: Artificial
<220> FEATURE:
<223> OTHER INFORMATION: nucleic acid sequence of the long fragment of
      CBSA

<400> SEQUENCE: 28
ctccttcaac gaagtgggtc cttcaacgaa gtgggtctc                              39

<210> SEQ ID NO 29
<211> LENGTH: 17
<212> TYPE: DNA
<213> ORGANISM: Artificial
<220> FEATURE:
<223> OTHER INFORMATION: nucleic acid sequence of the short fragment of
      CBSA

<400> SEQUENCE: 29
gagacaagga caaggag                                                     17
```